United States Patent [19]
Lal et al.

[11] Patent Number: 6,057,140
[45] Date of Patent: May 2, 2000

[54] HUMAN SCAD FAMILY MOLECULES

[75] Inventors: Preeti Lal, Santa Clara; Karl J. Guegler, Menlo Park; Gina A. Gorgone, Palo Alto; Neil C. Corley, Mountain View; Mariah R. Baughn, San Leandro; Henry Yue, Sunnyvale, all of Calif.

[73] Assignee: Incyte Pharmaceuticals, Inc., Palo Alto, Calif.

[21] Appl. No.: 09/109,205

[22] Filed: Jun. 30, 1998

[51] Int. Cl.[7] .............................. C12N 9/04; C12N 1/20; C12N 15/00; C12Q 1/68; C07H 21/02
[52] U.S. Cl. ........................ 435/190; 435/6; 435/252.3; 435/320.1; 536/23.1; 536/23.2; 536/23.5
[58] Field of Search ................................ 435/190, 252.3, 435/6, 320.1; 536/23.2, 23.5, 23.1; 475/320.1

[56] References Cited

U.S. PATENT DOCUMENTS 5,731,195  3/1998  Simon et al. ........................ 435/252.3

OTHER PUBLICATIONS

Koivuranta et al. Isolation and characterization of cDNA for human 120 kDa mitochondrial 2,4–dienoyl–coenzyme A reductase. Biochem. J. 304:787–792, 1994.

Adams et al. Genebank Accession Number AA295728, Apr. 1997.

Hillier et al. Genebank Accession Number AA152345, Dec. 1996.

Watson et al. Recombinant DNA, 2nd edition. WH Freeman and Company, New York, pp. 453–454, Feb. 1994.

Baker, M.E., "enoyl–acyl–carrier–protein reductase and *Mycobacterium tuberculosis* InhA do not conserve the Tyr–Xaa–Xaa–Lys motif in mammalian 11β–and 17βhyroxysteriod dehydrogenase", *Biochem. J.*, 309: 1029–1030 (1995).

Jornvall, H. et al., "Short–Chain Dehydrogenase/Reductase (SDR)", *Biochemistry*, 34: 6003–6013 (1995).

Duax, W.L. and D. Ghosh, "Structure and function of steroid dehydrogenases involved in hypertension, fertility, and cancer", *Steroids*, 62: 95–100 (1997).

Roe, C.R., et al., "2, 4–Dienoyl–Coenzyme a Reductase Deficiency: A Possible New Disorder of Fatty Acid Oxidation", *J. Clin. Invest.*, 85:1703–1707 (1990).

Chai, Xiyun, et al., "Cloning of a cDNA for Liver Microsomal Retinol Dehydrogenase", *J. Biol. Chem.*, 270: 3900–3904 (1995).

Kunau, W.H. and P. Dommes, "Degradation of Unsaturated Fatty Acids", *Eur. J. Biochem.*, 91: 533–544 (1978).

Simon, A. et al., (Direct Submission), GenBank Sequence Database (Accession U43559), National Center for Biotechnology Information, National Library of Medicine, Bethesda, Maryland, 20894, (GI 1616643; GI 1616654).

Chai, X. et al., (Direct Submission), GenBank Sequence Database (Accession U18762), National Center for Biotechnology Information, National Library of Medicine, Bethesda, Maryland, 20894, (GI 841196; GI 841197).

Ding, J.H. et al., (Direct Submission), GenBank Sequence Database (Accession U49352), National Center for Biotechnology Information, National Library of Medicine, Bethesda, Maryland, 20894, (GI 1574999; GI 1575000).

*Primary Examiner*—Bradley Sisson
*Assistant Examiner*—Devesh Srivastava
*Attorney, Agent, or Firm*—Incyte Pharmaceuticals, Inc.

[57] ABSTRACT

The invention provides human SCAD family molecules (HSFM) and polynucleotides which identify and encode HSFM. The invention also provides expression vectors, host cells, antibodies, agonists, and antagonists. The invention also provides methods for diagnosing, treating, or preventing disorders associated with expression of HSFM.

11 Claims, 13 Drawing Sheets

FIGURE 1A

```
5'                                                                                          
   GC CAG GGA CTC GGG TGC CTG GGG CAG ACG AGG CCG GCT TCT CCG CGG ACA GCT
                8         17        26        35        44        53

AGG GAG AGT GTC CTG GGT GTC AGC AAC ATG TCT TTC AAC CTG CAA TCA TCA
                62        71        80        89        98       107
                                       M   S   F   N   L   Q   S   S

AAG AAA CTG TTC ATT TTC TTA GGA AAA TCA CTG TTT AGT CTT GAG GCT ATG
               116       125       134       143       152       161
    K   K   L   F   I   F   L   G   K   S   L   F   S   L   E   A   M

ATT TTT GCC TTA CTC CCA AAG CGG AAG AAC CGG GTT GCT GGT GAA ATA GTC CTC
               170       179       188       197       206       215
    I   F   A   L   L   P   K   R   K   N   R   V   A   G   E   I   V   L

ATC ACA GGT GCT GGA AGT GGA AGG CTC TTA GCC TTG CAG TTT GCC CGG
               224       233       242       251       260       269
    I   T   G   A   G   S   G   R   L   L   A   L   Q   F   A   R

CTG GGA TCT GTT CTT CTC TGG GAT ATC AAT AAG GAG GGG AAT GAG GAA ACA
               278       287       296       305       314       323
    L   G   S   V   L   L   W   D   I   N   K   E   G   N   E   E   T
```

```
TGT AAG ATG GCT CGG GAA GCT GGA GCC ACA AGA GTG CAC GCC TAT ACC TGC GAT
 C   K   M   A   R   E   A   G   A   T   R   V   H   A   Y   T   C   D
332                 341             350             359             368             377

TGC AGC CAA AAG GAA GTG TAT AGA GTA GCC GAC CAG GTT AAA GAA AAA GAA GTC
 C   S   Q   K   E   V   Y   R   V   A   D   Q   V   K   E   K   E   V
386                 395             404             413             422             431

GGC GAT GTT TCC ATC CTA ATC AAC AAT GCC GGA ATC GTA ACA GGC AAA AAG TTC
 G   D   V   S   I   L   I   N   N   A   G   I   V   T   G   K   K   F
440                 449             458             467             476             485

CTT GAC TGT CCA GAT GAG CTT ATG GAA AAG TCA CCT GCT ATT GCT AAT TTC AAA GCA
 L   D   C   P   D   E   L   M   E   K   S   P   A   I   A   N   F   K   A
494                 503             512             521             530             539

CAT TTA TGG ACT TAT AAA GCC TTT CTA CCT GCT GTG ATT GCT AAT GAC CAT GGA
 H   L   W   T   Y   K   A   F   L   P   A   V   I   A   N   D   H   G
548                 557             566             575             584             593

CAT TTG GTT TGC ATT TCA AGT TCA GCT GGA TTA AGT GGA GTA AAT GGG CTG GCA
 H   L   V   C   I   S   S   S   A   G   L   S   G   V   N   G   L   A
602                 611             620             629             638             647
```

FIGURE 1B

```
      656             665             674             683             692             701
GAT   TAC   TGT   GCA   AGT   AAA   TTT   GCA   TTT   GGG   TTT   GCT   GAA   TCT   GTA   TTT   GTA
 D     Y     C     A     S     K     F     A     F     G     F     A     E     S     V     F     V 710             719             728             737             746             755
GAA   ACA   TTT   GTC   CAA   AAA   CAA   AAG   GGG   ATC   AAA   ACC   ACG   ATT   GTG   TGC   CCC   TTT
 E     T     F     V     Q     K     Q     K     G     I     K     T     T     I     V     C     P     F 764             773             782             791             800             809
TTT   ATA   AAA   ACT   GGA   ATG   TTT   GAA   GGT   TGT   ACT   ACA   GGC   T     GT   CCT   TCT   CTG   TTG
 F     I     K     T     G     M     F     E     G     C     T     T     G     C     P     S     L     L 818             827             836             845             854             863
CCA   ATT   CTG   GAA   TAT   GCA   AAA   TAT   GCA   GTT   GAA   AAA   ATA   GTA   GAA   GCT   ATT   CTA   CAA
 P     I     L     E     Y     A     K     Y     A     V     E     K     I     V     E     A     I     L     Q 872             881             890             899             908             917
ATG   TAC   TTG   TAT   ATG   CCA   AAG   TTG   TTA   TAC   TTC   ATG   GTA   GAA   ATG   TTT   CTT   AAA
 M     Y     L     Y     M     P     K     L     L     Y     F     M     V     E     M     F     L     K 926             935             944             953             962             971
AGC   TTT   TTG   CCC   CTC   AAG   ACA   GGA   CTG   CTT   ATA   GCT   GAC   TAT   TTG   GGC   ATC   CTT
 S     F     L     P     L     K     T     G     L     L     I     A     D     Y     L     G     I     L
```

FIGURE 1C

```
                980         989         998        1007        1016        1025
CAT GCA ATG GAT GGC TTT GTT GAC CAA AAG AAG CTC TAA AGA CCA ACT CTA
 H   A   M   D   G   F   V   D   Q   K   K   K   L 1034        1043        1052        1061        1070        1079
TGG CTA AGG TCA TCT GAT ACA CAG TGT TAC ATA ATG CGT ACT TCA ATG AAG AAA 1088        1097        1106        1115        1124        1133
AGT ATT TTT GTC TGA CAG TGG AAT ATA TCT GGA GAC CAC AAG TAC CAC TCC TAT 1142        1151        1160        1169        1178        1187
TCT GTT ATC TGG ACT AGA ATT TTC AAT CAA TGT GTT TGA AAA TAA TGT TGC TAT 1196        1205        1214        1223        1232        1241
CAC CTA TTT GGT TGA GTT TTG GTT TTT TCT TTT TTT TCT TTC CAA AAA TAA 1250        1259        1268
AGA CAG CCC ATT TTT GTC ATT TCC ATT A 3'
```

FIGURE 1D

```
5'  C TCC CGG TTC CAG GCG AGT TCG CAG CTG CGC GCC GGG TCC TGG AGG CCG AGG
              7          16          25          34          43          52

CCG CTC CCG CCC GTT GTC CCC GCA GAC GTC CCC GAC AGC GCC ATG GCC CAG CCG
     P   L   P   P   V   V   P   A   D   V   P   D   S   A   M   A   Q   P
             61          70          79          88          97         106

CCG GAC GTG GAG GGG GAC GAC TGT CTC CCC GCG TAC CGC CAC CTC TTC TGC
     P   D   V   E   G   D   D   C   L   P   A   Y   R   H   L   F   C
            115         124         133         142         151         160

CCG GAC CTG CGG GAC AAA GTG GCC TTC ATC ACA GGA GGC TCT GGG ATT
     P   D   L   R   D   K   V   A   F   I   T   G   G   S   G   I
            169         178         187         196         205         214

GGG TTC CGG ATT GCT GAG ATT TTC ATG CGG CAC GGC TGC CAT ACG GTG ATT GCC
     G   F   R   I   A   E   I   F   M   R   H   G   C   H   T   V   I   A
            223         232         241         250         259         268

AGT AGG AGC CTG CCG CGA GTG CTG CCG ACG GCC GCC AGG AAG CTG GCT GGG GCC ACC
     S   R   S   L   P   R   V   L   P   T   A   A   R   K   L   A   G   A   T
            277         286         295         304         313         322
```

FIGURE 2A

```
          331             340             349             358             367             376
GGC CGG TGC CTC TCT ATG GAC GTC CGA GCG CCC CCA GCT GTC ATG
 G   R   C   L   S   M   D   V   R   A   P   P   A   V   M 385             394             403             412             421             430
GCC GCC GTG GAC CAG GCT CTG AAG GAG TTT GGC AGA ATC CTC ATT AAC
 A   A   V   D   Q   A   L   K   E   F   G   R   I   L   I   N 439             448             457             466             475             484
TGT GCG GGG AAC TTC CTG TGC CCC GCT GGC TTG TCC TTC AAC GCC TTC
 C   A   G   N   F   L   C   P   A   G   L   S   F   N   A   F 493             502             511             520             529             538
AAG ACC GTG ATG GAC ATC GAT ACC AGC GGC ACC TTC AAT GTG TCT CGT GTG CTC
 K   T   V   M   D   I   D   T   S   G   T   F   N   V   S   R   V   L 547             556             565             574             583             592
TAT GAG AAG TTC TTC CGG GAC CAC GGA GGG GTG ATC GTG AAC ATC ACT GCC ACC
 Y   E   K   F   F   R   D   H   G   G   V   I   V   N   I   T   A   T 601             610             619             628             637             646
CTG GGG AAC CGG GGG CAG CAG GCG CTC CAT GTG GCA GGC TCC GCC AAG GCC GCT
 L   G   N   R   G   Q   Q   A   L   H   V   A   G   S   A   K   A   A
```

FIGURE 2B

| | 655 | | | 664 | | | 673 | | | 682 | | | 691 | | | 700 |
|---|---|---|---|---|---|---|---|---|---|---|---|---|---|---|---|---|
| GTG | GAC | GCG | ATG | ACG | CGG | CAC | TTG | GCT | GTG | GAG | TGG | GGT | CCC | CAA | AAC | ATC | CGC |
| V | D | A | M | T | R | H | L | A | V | E | W | G | P | Q | N | I | R |

| | 709 | | | 718 | | | 727 | | | 736 | | | 745 | | | 754 |
|---|---|---|---|---|---|---|---|---|---|---|---|---|---|---|---|---|
| GTC | AAC | AGC | CTC | GCC | CCT | GGC | ATC | AGT | GGC | ACA | GAG | GGG | CTC | CGG | CGA | CTG |
| V | N | S | L | A | P | G | I | S | G | T | E | G | L | R | R | L |

| | 763 | | | 772 | | | 781 | | | 790 | | | 799 | | | 808 |
|---|---|---|---|---|---|---|---|---|---|---|---|---|---|---|---|---|
| GGT | GGC | CCT | CAG | GCC | AGC | CTG | AGC | ACC | AAG | GTC | ACT | GCC | CCG | CTG | CAG | AGG |
| G | G | P | Q | A | S | L | S | T | K | V | T | A | P | L | Q | R |

| | 817 | | | 826 | | | 835 | | | 844 | | | 853 | | | 862 |
|---|---|---|---|---|---|---|---|---|---|---|---|---|---|---|---|---|
| CTG | GGG | AAC | AAG | ACC | GAG | ATC | GCC | CAC | AGC | GTG | ACT | CTC | TAC | CTG | AGC | CCT |
| L | G | N | K | T | E | I | A | H | S | V | T | L | Y | L | S | P |

| | 871 | | | 880 | | | 889 | | | 898 | | | 907 | | | 916 |
|---|---|---|---|---|---|---|---|---|---|---|---|---|---|---|---|---|
| CTG | GGG | AAC | AAG | ACC | GAG | ATC | GCC | CAC | AGC | GTG | ACT | CTC | TAC | CTG | AGC | CCT |

Note: reading from image:

| | 871 | | | 880 | | | 889 | | | 898 | | | 907 | | | 916 |
|---|---|---|---|---|---|---|---|---|---|---|---|---|---|---|---|---|
| GCT | TCC | TAC | GTG | ACG | GGG | GCC | GTG | CTG | GCC | CTC | TAC | CTG | GCA | AGC | CCT | ACG |
| A | S | Y | V | T | G | A | V | L | A | L | Y | L | A | S | P | T |

| | 925 | | | 934 | | | 943 | | | 952 | | | 961 | | | 970 |
|---|---|---|---|---|---|---|---|---|---|---|---|---|---|---|---|---|
| TTC | CCA | AAC | GGT | GTC | AAA | GGG | CTG | CCG | GAT | TTC | GCA | TCC | TTC | TCT | GCT | AAG | CTC |
| F | P | N | G | V | K | G | L | P | D | F | A | S | F | S | A | K | L |

FIGURE 2C

```
         979        988        997       1006       1015       1024
TAG GAA TCT TCC GGC CGC TGC TTC CTG CCG CCT CAC TCA GCC AGG TGG AGA GCA 1033       1042       1051       1060       1069       1078
CCA ATC TGA ACC AGC AAT GCC CCA TGC AGC CCA GCC CCT CCT CTG AAC ACT CAG CTA 1087       1096       1105       1114       1123       1132
TTA CTG CGC TTT CCC TCC CCA CGG CCC CAA CTC CAG GGC AGG AGC AAC TGG ACA 1141       1150       1159       1168       1177       1186
GTG GGC CTG GCC CGT GGA GCT GCC ACG CAG GTG CCT GAG GGC CAG GTG CCA CGC 1195       1204       1213       1222       1231       1240
AGG TGT CTG AGG ACC AGG TGC CAC GCA GGT GGT GGG GGT ACA GAC AAG ATG CTG 1249       1258       1267       1276       1285       1294
GGA TGT CCC CTG CCC CAT GGT CAA GGG TGT CCT GCC TGC CTG GGT CCA GGG CCT
```

FIGURE 2D

```
            1303          1312          1321          1330          1339          1348
GAG GGA GCC ACA TGG ATC CCG AGA CTT GTG TTC TCT TGG CTG AAA ACA CTG AGG 1357          1366          1375          1384          1393          1402
TGC TCC CAT CTG TGC GTG GCC CAT GAG CTG GGA TGG TCC TCC AGC TGC CCA CAA 1411          1420          1429          1438          1447          1456
GGT CCG CCC CTC TGT CTC TGC ACC ACC TGT TTG CAT AAA CAC ACT TTG CTA CAA 1465          1474          1483          1492          1501          1510
TCT TGC TAG TGC GTT TTC TTA AAA GAT AAT CTA TTT ACT GTA AAA ATA AAT TGG 1519          1528          1537          1546
ACT TTG CAA AAG CTT TTA GAA GGA AAA GAA AGA GGA TTA AAG GG 3'
```

```
176 SSSAGLSGVNGLADYCASKFAAFGFAESVF         1511003
162 TSVLGRLAANG-GGYCVSKFGLEAFSDSLR         GI 1616654
163 ASTMGRMSLVG-GGYCISKYGVEAFSDSLR         GI 841197

206 VETFVQKQKGIKTTIVCPFFIKTGM----          1511003
191 RDV---AHFGIRVSIVEPGFFRTPVTNLES         GI 1616654
192 REL---TYFGVKVAHIEPGGFKTNVTNMER         GI 841197

231 FEGCTTGC-PSLLPILEPKYA--------          1511003
218 LEKTLQACWARLPPATQAHYGGAFLTKYLK         GI 1616654
219 LSDNLKKLWDQTTEEVKEIYGEKFQDSYMK         GI 841197

251 -VEKIVEAI--------LQEKMYLYMP            1511003
248 MQQRIMNLICDPDLTKVSRCLEHALTARHP         GI 1616654
249 AMESLVN-TCSGDLSLVTDCMEHALTSCHP         GI 841197

269 KLLYFMMFLKSFLPLKTGLLIADYLGILHA         1511003
278 RTRYSPGWDAKLLWLPASYLPASLVDAVLT         GI 1616654
278 RTRYSPGWDAKFFYLPMSYLPTFLSDAVIH         GI 841197

299 MDGFVDQKKKL                            1511003
308 WVLPKPAQAVY                            GI 1616654
308 WGSVKPARAL                             GI 841197
```

FIGURE 3B

```
1    MAQPPP---DVEGD-DCLPAYRHLFC------                              1810320
1    MKLPARVFFTLGSRLPCGLAPRRFFSYGTK                                GI 1575000

23   ------------------------PDLLRDK                               1810320
31   ILYQNTEALQSKFFSPLQKAMLPPNSFQGK                                GI 1575000

30   VAFITGGGSGIGFRIAEIFMRHGCHTVIAS                                1810320
61   VAFITGGGTGLGKGMTTLLSSLGAQCVIAS                                GI 1575000

60   RSLPRVLTAARKLAGATGRRCLPLSMDVRA                                1810320
91   RKMDVLKATAEQISSQTGNKVHAIQCDVRD                                GI 1575000

90   PPAVMAAVDQALKEFGRIDILINCAAGNFL                                1810320
121  PDMVQNTVSELIKVAGHPNIVINNAAGNFI                                GI 1575000

120  CPAGALSFNAFKTVMDIDTSGTFNVSRVLY                                1810320
151  SPTERLSPNAWKTITDIVLNGTAFVTLEIG                                GI 1575000

150  EKFFRDH-GGVIVNITATLGNRGQALQVHA                                1810320
181  KQLIKAQKGAAFLSITTIYAETGSGFVVPS                                GI 1575000
```

HUMAN SCAD FAMILY MOLECULES

FIELD OF THE INVENTION

This invention relates to nucleic acid and amino acid sequences of human SCAD family molecules and to the use of these sequences in the diagnosis, treatment, and prevention of disorders associated with cell proliferation, inflammation, and fatty acid and steroid metabolism.

BACKGROUND OF THE INVENTION

The short-chain alcohol dehydrogenases (SCADs) are a diverse family of oxidoreductase enzymes. SCAD family members are involved in all aspects of cell biochemistry and physiology, including metabolism of sugar, synthesis or degradation of fatty acids, and synthesis or degradation of glucocorticoids, estrogens, androgens, and prostaglandins $E_2$ and F2α, SCADs are found in bacteria, plants, invertebrates, and vertebrates. Alignment of the different family members reveals large homologous regions and clustered similarities indicating sites of structural and functional importance. Some of these sites are associated with a type of coenzyme-binding domain, but similarity between family members extends beyond this domain. Family members typically show only about 15% to 30% identity between enzyme pairs. Over one third of the conserved residues are glycine residues, showing the importance of conformational and spatial restrictions. (Baker, M. E. (1995) Biochem. J. 309: 1029–1030; and Jomvall, H. et al. (1995) Biochemistry 34: 6003–6013.) SCAD family members show different subcellular distributions. For example, 2,4-dienoyl-CoA reductase is located in the mitochondria, whereas retinol dehydrogenase is located in microsomes.

The SCAD family can be divided into two groups based on the arrangement of two conserved structural motifs. The first group contains a highly conserved pentapeptide, containing a tyrosine and a lysine, separated by any three amino acid residues, at about residue 150 in a 250-residue dehydrogenase. The tyrosine and lysine residues, which are absolutely conserved within this group, are likely to be important in catalysis. Support for the importance of these two residues comes from mutagenesis studies with Drosophila alcohol dehydrogenase, human 15-hydroxyprostaglandin dehydrogenase, and human 11β-hydroxysteroid and 17β-hydroxysteroid dehydrogenases. (Baker, supra.) The AMP-binding domain at the N-terminus, which consists of a hydrophobic pocket containing three glycine residues in a seven amino acid sequence, is also highly conserved in this group. (Baker, supra.)

The second group lacks either the tyrosine or the lysine in the pentapeptide motif. For example, the tyrosine residue is replaced by a methionine in *E. coli* enoyl-acyl-carrier protein (EnvM), by serine in rat and human 2,4-dienoyl-CoA reductases, and by valine in *S. cerevisiae* sporulation specific protein (SPX19). Some members of this group also have differences in the AMP-binding domain, including an insertion of two residues and poor conservation of the second and third glycine residues. These changes do not seem to affect the enoyl-CoA reductase activity of the proteins, though in the case of EnvM $NAD^+$ and substrate must bind simultaneously. (Baker, supra.)

The members of the SCAD family share a common function, utilizing $NAD^+$ or NADP as a cofactor in oxidation-reduction reactions, but differ in their substrate specificity. For example, 17-β-hydroxysteroid dehydrogenase interconverts estrone and estradiol, and androstenedione and testosterone. 2,4-dienoyl-CoA reductase partici- pates in the metabolism of unsaturated fatty acids, and 15-hydroxyprostaglandin dehydrogenase is the main enzyme in prostaglandin degradation. Retinol dehydrogenase catalyzes the primary rate limiting step in retinoic acid synthesis, and 11-cis-retinol dehydrogenase catalyzes the final step in the biosynthesis of 11-cis-retinaldehyde, the universal chromophore of visual pigments.

SCAD involvement in fatty acid and steroid metabolism implicates members of the SCAD family in a variety of disorders. Steroid dehydrogenases, such as the hydroxysteroid dehydrogenases, are involved in hypertension, fertility, and cancer. (Duax, W. L. and Ghosh, D. (1997) Steroids 62: 95–100.) Reduction in 2,4-dienoyl-CoA reductase activity has been associated with hyperlysinemia and hypocarnitinemia. (Roe, C. R. et al. (1990) J. Clin. Invest. 85: 1703–1707.) Retinoic acid, a regulator of differentiation and apoptosis, has been shown to down-regulate genes involved in cell proliferation and inflammation. (Chai, X. et al. (1995) J. Biol. Chem. 270: 3900–3904.)

The discovery of new human SCAD family molecules and the polynucleotides encoding them satisfies a need in the art by providing new compositions which are useful in the diagnosis, treatment, and prevention of disorders associated with proliferation, inflammation, and fatty acid and steroid metabolism.

SUMMARY OF THE INVENTION

The invention features substantially purified polypeptides, human SCAD family molecules, referred to collectively as "HSFM" and individually as "HSFM-1" and "HSFM-2." In one aspect, the invention provides a substantially purified polypeptide comprising an amino acid sequence selected from the group consisting of SEQ ID NO:1, SEQ ID NO:2, a fragment of SEQ ID NO:1, and a fragment of SEQ ID NO:2.

The invention further provides a substantially purified variant having at least 90% amino acid identity to the amino acid sequences of SEQ ID NO:1 or SEQ ID NO:2, or to a fragment of either of these sequences. The invention also provides an isolated and purified polynucleotide encoding the polypeptide comprising an amino acid sequence selected from the group consisting of SEQ ID NO:1, SEQ ID NO:2, a fragment of SEQ ID NO:1, and a fragment of SEQ ID NO:2. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, a fragment of SEQ ID NO:1, and a fragment of SEQ ID NO:2, as well as an isolated and purified polynucleotide having a sequence which is complementary to the polynucleotide encoding the polypeptide comprising the amino acid sequence selected from the group consisting of SEQ ID NO:1, SEQ ID NO:2, a fragment of SEQ ID NO:1, and a fragment of SEQ ID NO:2.

The invention also provides an isolated and purified polynucleotide comprising a polynucleotide sequence selected from the group consisting of SEQ ID NO:3, SEQ ID NO:4, a fragment of SEQ ID NO:3, and a fragment of SEQ ID NO:4. The invention further provides an isolated and purified polynucleotide variant having at least 90% polynucleotide sequence identity to the polynucleotide sequence comprising a polynucleotide sequence selected from the group consisting of SEQ ID NO:3, SEQ ID NO:4, a fragment of SEQ ID NO:3, and a fragment of SEQ ID NO:4, as well as an isolated and purified polynucleotide having a sequence which is complementary to the polynucleotide comprising a polynucleotide sequence selected from the group consisting of SEQ ID NO:3, SEQ ID NO:4, a fragment of SEQ ID NO:3, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:2, a fragment of SEQ ID NO: 1, and a fragment of SEQ ID NO:2. In another aspect, the expression vector is contained within a host cell.

The invention also provides a method for producing a polypeptide comprising the amino acid sequence selected from the group consisting of SEQ ID NO:1, SEQ ID NO:2, a fragment of SEQ ID NO:1, and a fragment of SEQ ID NO:2, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, a fragment of SEQ ID NO:1, and a fragment of SEQ ID NO:2 in conjunction with a suitable pharmaceutical carrier.

The invention further includes a purified antibody which binds to a polypeptide comprising the amino acid sequence selected from the group consisting of SEQ ID NO:1, SEQ ID NO:2, a fragment of SEQ ID NO:1, and a fragment of SEQ ID NO:2, as well as a purified agonist and a purified antagonist to the polypeptide. The invention also provides a method for treating or preventing a cell proliferative disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:2, a fragment of SEQ ID NO:1, and a fragment of SEQ ID NO:2.

The invention also provides a method for treating or preventing an inflammatory disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:2, a fragment of SEQ ID NO:1, and a fragment of SEQ ID NO:2.

The invention also provides a method for treating or preventing a fatty acid and steroid metabolic disorder, the method comprising administering to a subject in need of such treatment an effective amount of a pharmaceutical composition comprising a substantially purified polypeptide having an amino acid sequence selected from the group consisting of SEQ ID NO: 1, SEQ ID NO:2, a fragment of SEQ ID NO:1, and a fragment of SEQ ID NO:2.

The invention also provides a method for detecting a polynucleotide encoding the polypeptide comprising the amino acid sequence selected from the group consisting of SEQ ID NO:1, SEQ ID NO:2, a fragment of SEQ ID NO:1, and a fragment of SEQ ID NO:2 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:2, a fragment of SEQ ID NO:1, and a fragment of SEQ ID NO:2 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the method further comprises amplifying the polynucleotide prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:3) of HSFM-1. The alignments were produced using MacDNASIS PRO™ software (Hitachi Software Engineering Co. Ltd., San Bruno, Calif.).

FIGS. 2A, 2B, 2C, 2D, and 2E show the amino acid sequence (SEQ ID NO:2) and nucleic acid sequence (SEQ ID NO:4) of HSFM-2.

FIGS. 3A and 3B show the amino acid sequence alignments among HSFM-1 (1511003; SEQ ID NO:1), human 11-cis-retinol dehydrogenase (GI 1616654; SEQ ID NO:17) and rat retinol dehydrogenase (GI 841197; SEQ ID NO:18)

FIGS. 4A and 4B show the amino acid sequence alignments between HSFM-2 (1810320; SEQ ID NO:2) and human 2,4-dienoyl-CoA reductase (GI 1575000; SEQ ID NO:19). Sequence alignments were produced using the multisequence alignment program of LASERGENE™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HSFM," as used herein, refers to the amino acid sequences, or variant thereof, of substantially purified HSFM obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HSFM, increases or prolongs the duration of the effect of HSFM. Agonists may include proteins, nucleic acids, carbohydrates, or any other molecules which bind to and modulate the effect of HSFM.

An "allelic variant," as this term is used herein, is an alternative form of the gene encoding HSFM. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HSFM, as described herein, include those sequences with deletions, insertions, or substitutions of different nucleotides, resulting in a polynucleotide the same as HSFM or a polypeptide with at least one functional characteristic of HSFM. Included within this definition are polymorphisms which may or may not be readily detectable using a particular oligonucleotide probe of the polynucleotide encoding HSFM, and improper or unexpected hybridization to allelic variants, with a locus other than the normal chromosomal locus for the polynucleotide sequence encoding HSFM. The encoded protein may also be "altered," and may contain deletions, insertions, or substitutions of amino acid residues which produce a silent change and result in a functionally equivalent HSFM. Deliberate amino acid substitutions may be made on the basis of similarity in polarity, charge, solubility, hydrophobicity, hydrophilicity, and/or the amphipathic nature of the residues, as long as the biological or immunological activity of HSFM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HSFM which are preferably at least 5 to about 15 amino acids in length, most preferably at least 14 amino acids, and which retain some biological activity or immunological activity of HSFM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer. a Laboratory Manual,* Cold Spring Harbor Press, Plainview, N.Y., pp. 1–5.)

The term "antagonist," as it is used herein, refers to a molecule which, when bound to HSFM, decreases the amount or the duration of the effect of the biological or immunological activity of HSFM. Antagonists may include proteins, nucleic acids, carbohydrates, antibodies, or any other molecules which decrease the effect of HSFM.

As used herein, the term "antibody" refers to intact molecules as well as to fragments thereof, such as Fab, $F(ab')_2$, and Fv fragments, which are capable of binding the epitopic determinant. Antibodies that bind HSFM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HSFM, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "5' A-G-T 3' " binds to the complementary sequence "3'T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding HSFM or fragments of HSFM may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (The Perkin-Elmer Corp., Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acid, the same or related to a nucleic acid sequence encoding HSFM, by Northern analysis is indicative of the presence of nucleic acids encoding HSFM in a sample, and thereby correlates with expression of the transcript from the polynucleotide encoding HSFM.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73: 237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183: 626–645.) Identity between sequences can also be determined by other methods known in the art, e.g., by varying hybridization conditions. "Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15: 345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_o t$ or $R_o t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HSFM. For example, modulation may cause an increase or a decrease in protein activity, binding characteristics, or any other biological, functional, or immunological properties of HSFM.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8: 53–63.)

The term "sample," as used herein, is used in its broadest sense. A biological sample suspected of containing nucleic acids encoding HSFM, or fragments thereof, or HSFM itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HSFM polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The term "variant," when used in the context of a polynucleotide sequence, may encompass a polynucleotide sequence related to HSFM. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human SCAD family molecules (HSFM), the polynucleotides encoding HSFM, and the use of these compositions for the diagnosis, treatment, or prevention of disorders associated with cell proliferation, inflammation, and fatty acid and steroid metabolism.

Nucleic acids encoding the HSFM-1 of the present invention were first identified in Incyte Clone 1511003 from the lung cDNA library (LUNGNOT14) using a computer search, e.g., BLAST, for amino acid sequence alignments. A consensus sequence, SEQ ID NO:3, was derived from the following overlapping and/or extended nucleic acid sequences: Incyte Clones 2921571H1 (SININOT04), 1511003F6, 1511003H1, and 1511003T6 (LUNGNOT14), and 2722958F6 (LUNGTUT10).

Figure 3A:
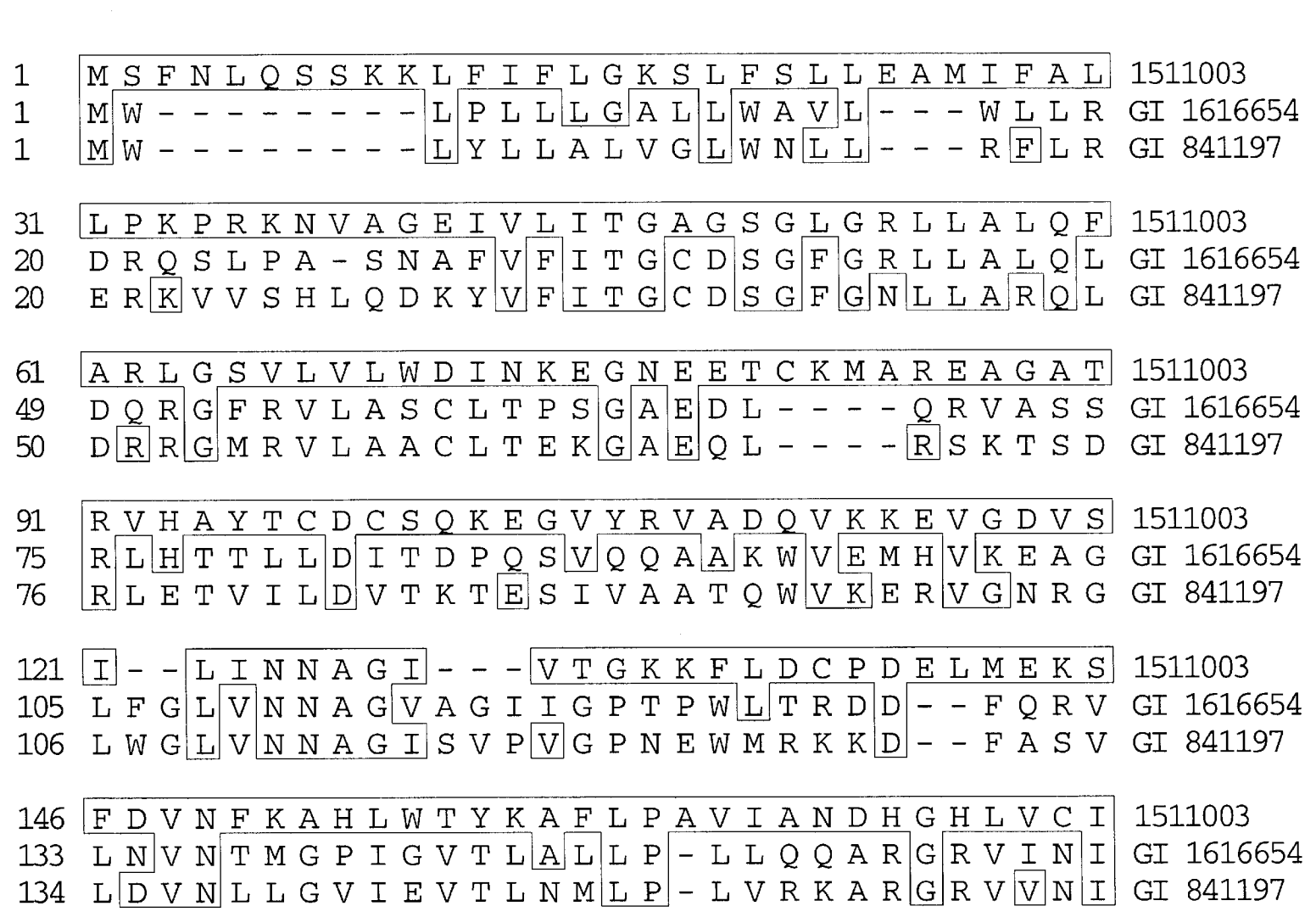

In one embodiment, the invention encompasses a polypeptide comprising the amino acid sequence of SEQ ID NO:1, as shown in FIGS. 1A, 1B, 1C, and ID. HSFM-1 is 309 amino acids in length and has a potential amidation site at residue T1 30; two potential casein kinase II phosphorylation sites at residues S21 and S100; and six potential protein kinase C phosphorylation sites at residues S7, S8, T80, S100, T130, and T156. BLOCKS identifies significant sequence identity with short chain alcohol dehydrogenases from residues E41 through G53, G117 through G127, and G170 through E207. PRINTS identifies significant sequence identitiy with short chain alcohol dehydrogenases from residues G117 through I128, and Y190 through F209. Profilescan identifies a short-chain alcohol dehydrogenase family signature from residues D168 through P223. PFAM identifies significant sequence identity with short chain alcohol dehydrogenases. HSFM-1 contains the canonical AMP-binding domain and catalytic site of short chain alcohol dehydrogenases at residues 47–53 and 190–194, respectively. As shown in FIGS. 3A and 3B, HSFM-1 has chemical and structural similarity with human 11-cis-retinol dehydrogenase (GI 1616654; SEQ ID NO:17) and rat retinol dehydrogenase (GI 841197; SEQ ID NO:18). In particular, HSFM-1 shares 17% identity with human 11-cis-retinol dehydrogenase and 16% identity with rat retinol dehydrogenase. HSFM-1, human 11-cis-retinol dehydrogenase, and rat retinol dehydrogenase also have similar molecular mass (34.1 kDa, 35.0 kDa, and 35.7 kDa, respectively) and share canonical AMP-binding and catalytic domains. A region of unique sequence in HSFM-1 from about amino acid 151 to about amino acid 157 is encoded by a fragment of SEQ ID NO:3 from about nucleotide 534 to about nucleotide 554. Northern analysis shows the expression of this sequence in various libraries, at least 64% of which are proliferative or cancerous and at least 14% of which involve immune response. Of particular note is the expression of HSFM-1 in cardiovascular, gastrointestinal, reproductive, and nervous tissues.

Nucleic acids encoding the HSFM-2 of the present invention were first identified in Incyte Clone 1810320 from the prostate tumor cDNA library (PROSTUT12) using a computer search, e.g., BLAST, for amino acid sequence alignments. A consensus sequence, SEQ ID NO:4, was derived from the following overlapping and/or extended nucleic acid sequences: Incyte Clones 1515168H1 (PANCTUT01), 1810320H1(PROSTUT12), 1653184T6 (PROSTUT18), 1750778T6 (LIVRTUT01), 484767X17 (HNT2RAT01), and 2466459T6 (THYRNOT08) and shotgun sequence SAFC01552F1.

In another embodiment, the invention encompasses a polypeptide comprising the amino acid sequence of SEQ ID NO:2, as shown in FIGS. 2A, 2B, 2C, 2D, and 2E. HSFM-2 is 292 amino acids in length and has two potential casein kinase II phosphorylation sites at residues T132 and S212; four potential protein kinase C phosphorylation sites at residues T76, S180, S228, and S289; three potential N-glycosylation sites at residues N143, N162, and N241; and a C-terminal microbody targeting signal at residues $A_{290}$ KL. BLOCKS identifies significant sequence identity with short chain alcohol dehydrogenases from residues K29 through G41, G105 through A115, G158 through E195, and N200 through G209. PRINTS identifies significant sequence identity with short chain alcohol dehydrogenases from residues G105 through G116, and A178 through G197. PFAM identifies significant sequence identity with short chain alcohol dehydrogenases. HSFM-2 contains the canonical AMP-binding domain of short chain alcohol dehydrogenases at residues 35–41. As shown in FIGS. 4A and 4B, HSFM-2 has chemical and structural similarity with human 2,4-dienoyl-CoA reductase (GI 1575000; SEQ ID NO:19). In particular, HSFM-2 and human 2,4-dienoyl-CoA reductase share 31 % identity. HSFM-2 and human 2,4-dienoyl-CoA reductase share canonical AMP-binding domains and modified catalytic domains lacking the tyrosine residue (178–182 and 210–214 in HSFM-2 and human 2,4-dienoyl-CoA reductase, respectively). A region of unique sequence in HSFM-2 from about amino acid 149 to about amino acid 155 is encoded by a fragment of SEQ ID NO:4 from about nucleotide 539 to about nucleotide 559. Northern analysis shows the expression of this sequence in various libraries, at least 75% of which are proliferative or cancerous, at least 29% involve immune response. Of particular note is the expression of HSFM-2 in gastrointestinal, reproductive, and nervous tissues.

The invention also encompasses HSFM variants. A preferred HSFM variant is one which has at least about 80%, more preferably at least about 90%, and most preferably at least about 95% amino acid sequence identity to the HSFM amino acid sequence, and which contains at least one functional or structural characteristic of HSFM.

The invention also encompasses polynucleotides which encode HSFM. In a particular embodiment, the invention encompasses a polynucleotide sequence comprising the sequence of SEQ ID NO:3, which encodes an HSFM-1 as shown in FIGS. 1A, 1B, 1C, and 1D. In a further embodiment, the invention encompasses the polynucleotide sequence comprising the sequence of SEQ ID NO:4, which encodes an HSFM-2 as shown in FIGS. 2A, 2B, 2C, 2D, and 2E.

The invention also encompasses a variant of a polynucleotide sequence encoding HSFM. In particular, such a variant polynucleotide sequence will have at least about 70%, more preferably at least about 85%, and most preferably at least about 95% polynucleotide sequence identity to the polynucleotide sequence encoding HSFM. A particular aspect of the invention encompasses a variant of SEQ ID NO:3 which has at least about 70%, more preferably at least about 85%, and most preferably at least about 95% polynucleotide sequence identity to SEQ ID NO:3. The invention further encompasses a polynucleotide variant of SEQ ID NO:4 having at least about 70%, more preferably at least about 85%, and most preferably at least about 95% polynucleotide sequence identity to SEQ ID NO:4. Any one of the polynucleotide variants described above can encode an amino acid sequence which contains at least one functional or structural characteristic of HSFM.

It will be appreciated by those skilled in the art that as a result of the degeneracy of the genetic code, a multitude of polynucleotide sequences encoding HSFM, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HSFM, and all such variations are to be considered as being specifically disclosed.

Although nucleotide sequences which encode HSFM and its variants are preferably capable of hybridizing to the nucleotide sequence of the naturally occurring HSFM under appropriately selected conditions of stringency, it may be advantageous to produce nucleotide sequences encoding HSFM possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSFM and its derivatives without altering the encoded amino acid sequences include the production of RNA transcripts having more desirable properties, such as a greater half-life, than transcripts produced from the naturally occurring sequence.

The invention also encompasses production of DNA sequences which encode HSFM and HSFM derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HSFM or any fragment thereof.

Also encompassed by the invention are polynucleotide sequences that are capable of hybridizing to the claimed polynucleotide sequences, and, in particular, to those shown in SEQ ID NO:3, SEQ ID NO:4, a fragment of SEQ ID NO:3, or a fragment of SEQ ID NO:4, under various conditions of stringency. (See, e.g., Wahl, G. M. and S. L. Berger (1987) Methods Enzymol. 152: 399–407; Kimmel, A. R. (1987) Methods Enzymol. 152: 507–511.) For example, stringent salt concentration will ordinarily be less than about 750 mM NaCI and 75 mM trisodium citrate, preferably less than about 500 mM NaCI and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 $\mu$g/ml denatured salmon sperm DNA (ssDNA). In a most preferred embodiment, hybridization will occur at 42° C. in 250 mM NaCl, 25 mM trisodium citrate, 1 % SDS, 50 % formamide, and 200 $\mu$g/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCI and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1 % SDS. In a more preferred embodiment, wash steps will occur at 42° C. in 15 mM NaCl, 1.5 mM trisodium citrate, and 0.1 % SDS. In a most preferred embodiment, wash steps will occur at 68° C. in 15 mM NaCl, 1.5 mM trisodium citrate, and 0.1 % SDS. Additional variations on these conditions will be readily apparent to those skilled in the art.

Methods for DNA sequencing and analysis are well known in the art. The methods may employ such enzymes as the Klenow fragment of DNA polymerase I, SEQUENASE® (Amersham Pharmacia Biotech Ltd., Uppsala, Sweden), Taq polymerase (The Perkin-Elmer Corp., Norwalk, Conn.), thermostable T7 polymerase (Amersham Pharmacia Biotech Ltd., Uppsala, Sweden), or combinations of polymerases and proofreading exonucleases, such as those found in the ELONGASETM amplification system (Life Technologies, Inc., Rockville, Md.). Preferably, sequence preparation is automated with machines, e.g., the ABI CATALYST™ 800 (The Perkin-Elmer Corp., Norwalk, Conn.) or MICROLAB® 2200 (Hamilton Co., Reno, Nev.) systems, in combination with thermal cyclers. Sequencing can also be automated, such as by ABI PRISM™ 373 or 377 systems (The Perkin-Elmer Corp., Norwalk, Conn.) or the MEGABACE™ 1000 capillary electrophoresis system (Molecular Dynamics, Inc., Sunnyvale, Calif.). Sequences can be analyzed using computer programs and algorithms well known in the art. (See, e.g., Ausubel, supra, unit 7.7; and Meyers, R. A. (1995) *Molecular Biology and Biotechnology,* Wiley VCH, Inc, New York, N.Y.)

The nucleic acid sequences encoding HSFM may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2: 318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1: 111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19: 3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, (The Perkin-Elmer Corp., Norwalk, Conn.)), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HSFM may be cloned in recombinant DNA molecules that direct expression of HSFM, or fragments or functional equivalents thereof, in appropriate host cells. Due to the inherent degeneracy of the genetic code, other DNA sequences which encode substantially the same or a functionally equivalent amino acid sequence may be produced and used to express HSFM.

The nucleotide sequences of the present invention can be engineered using methods generally known in the art in order to alter HSFM-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HSFM may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, HSFM itself or a fragment thereof may be synthesized using chemical methods. For example, peptide synthesis can be performed using various solid-phase techniques. (See, e.g., Roberge, J. Y. et al. (1995) Science 269: 202–204.) Automated synthesis may be achieved using the ABI 431A Peptide Synthesizer (The Perkin-Elmer Corp., Norwalk, Conn.). Additionally, the amino acid sequence of HSFM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182: 392–421.) The composition of the synthetic peptides may be confirmed by amino acid analysis or by sequencing. (See, e.g., Creighton, T. (1984) *Proteins. Structures and Molecular Properties,* WH Freeman and Co., New York, N.Y.)

In order to express a biologically active HSFM, the nucleotide sequences encoding HSFM or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HSFM. Such elements may vary in their strength and specificity. Specific initiation signals may also be used to achieve more efficient translation of sequences encoding HSFM. Such signals include the ATG initiation codon and adjacent sequences, e.g. the Kozak sequence. In cases where sequences encoding HSFM and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20: 125–162.) Methods which are well known to those skilled in the art may be used to construct expression vectors containing sequences encoding HSFM and appropriate transcriptional and translational control elements. These methods include in vitro recombinant DNA techniques, synthetic techniques, and in vivo genetic recombination. (See, e.g., Sambrook, J. et al. (1989) *Molecular Cloning. A Laboratory Manual,* Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HSFM. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HSFM. For example, routine cloning, subcloning, and propagation of polynucleotide sequences encoding HSFM can be achieved using a multifunctional *E. coli* vector such as Bluescript® (Stratagene) or pSport1™ plasmid (GIBCO BRL). Ligation of sequences encoding HSFM into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264: 5503–5509.) When large quantities of HSFM are needed, e.g. for the production of antibodies, vectors which direct high level expression of HSFM may be used. For example, vectors containing the strong, inducible T5 or T7 bacteriophage promoter may be used.

Yeast expression systems may be used for production of HSFM. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153: 516–54; Scorer, C. A. et al. (1994) Bio/Technology 12: 181–184.)

Plant systems may also be used for expression of HSFM. Transcription of sequences encoding HSFM may be driven viral promoters, e.g., the 35S and 19S promoters of CaMV used alone or in combination with the omega leader sequence from TMV. (Takamatsu, N. (1987) EMBO J. 6: 307–311.) Alternatively, plant promoters such as the small subunit of RUBISCO or heat shock promoters may be used. (See, e.g., Coruzzi, G. et al. (1984) EMBO J. 3: 1671–1680; Broglie, R. et al. (1984) Science 224: 838–843; and Winter, J. et al. (1991) Results Probl. Cell Differ. 17: 85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding HSFM may be ligated into an adenovirus transcription/translation complex consisting of the late promoter and tripartite leader sequence. Insertion in a non-essential E1 or E3 region of the viral genome may be used to obtain infective virus which expresses HSFM in host cells. (See, e.g., Logan, J. and T. Shenk (1984) Proc. Natl. Acad. Sci. 81: 3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of HSFM in cell lines is preferred. For example, sequences encoding HSFM can be transformed into cell lines using expression vectors which may contain viral origins of replication and/or endogenous expression elements and a selectable marker gene on the same or on a separate vector. Following the introduction of the vector, cells may be allowed to grow for about I to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk or apr cells, respectively. (See, e.g., Wigler, M. et al. (1977) Cell 11: 223–232; and Lowy, I. et al. (1980) Cell 22: 817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77: 3567–3570; Colbere-Garapin, F. et al (1981) J. Mol. Biol. 150: 1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85: 8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55: 121–131.)

Although the presence/absence of marker gene expression suggests that the gene of interest is also present, the presence and expression of the gene may need to be confirmed. For example, if the sequence encoding HSFM is inserted within a marker gene sequence, transformed cells containing sequences encoding HSFM can be identified by the absence of marker gene function. Alternatively, a marker gene can be placed in tandem with a sequence encoding HSFM under the control of a single promoter. Expression of the marker gene in response to induction or selection usually indicates expression of the tandem gene as well.

In general, host cells that contain the nucleic acid sequence encoding HSFM and that express HSFM may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HSFM using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HSFM is preferred, but a competitive binding assay may be employed. These and other assays are well known in the art. (See, e.g., Hampton, R. et al. (1990) *Serological Methods. a Laboratory Manual,* APS Press, St Paul, Minn., Section IV; Coligan, J. E. et al. (1997 and periodic supplements) *Current Protocols in Immunology,* Greene Pub. Associates and Wiley-Interscience, New York, N.Y.; and Maddox, D. E. et al. (1983) J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSFM include oligolabeling, nick translation, end-labeling, or PCR amplification using a labeled nucleotide. Alternatively, the sequences encoding HSFM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HSFM may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HSFM may be designed to contain signal sequences which direct secretion of HSFM through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding HSFM may be ligated to a heterologous sequence resulting in translation of a fusion protein in any of the aforementioned host systems. For example, a chimeric HSFM protein containing a heterlogous moiety that can be recognized by a commercially available antibody may facilitate the screening of peptide libraries for inhibitors of HSFM activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HSFM encoding sequence and the heterologous protein sequence, so that HSFM may be cleaved away from the heterologous moiety following purification. Methods for fusion protein expression and purification are discussed in Ausubel, F. M. et al. (1995 and periodic supplements) *Current Protocols in Molecular Biology,* John Wiley & Sons, New York, N.Y., ch 10. A variety of commercially available kits may also be used to facilitate expression and purification of fusion proteins.

In a further embodiment of the invention, synthesis of radiolabeled HSFM may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HSFM may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (The Perkin-Elmer Corp., Norwalk, Conn.). Various fragments of HSFM may be synthesized separately and then combined to produce the full length molecule.

Therapeutics

Chemical and structural similarity exists among HSFM-1 and human 11-cis-retinol dehydrogenase (GI 1616654) and rat retinol dehydrogenase (GI 841197). In addition, HSFM-1 is expressed in proliferative and inflamed tissues. Therefore, HSFM-1 appears to play a role in disorders associated with cell proliferation, inflammation, and fatty acid and steroid metabolism.

Chemical and structural similarity exists between HSFM-2 and human 2,4-dienoyl-CoA reductase (GI 1575000). In addition, HSFM-2 is expressed in proliferative and inflamed tissues. Therefore, HSFM-2 appears to play a role in disorders associated with proliferation, inflammation, and fatty acid and steroid metabolism.

Therefore, in one embodiment, HSFM or a fragment or derivative thereof may be administered to a subject to treat or prevent a cell proliferative disorder. Such cell proliferative disorders can include, but are not limited to, actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HSFM or a fragment or derivative thereof may be administered to a subject to treat or prevent a cell proliferative disorder including, but not limited to, those described above.

In a further embodiment, a pharmaceutical composition comprising a substantially purified HSFM in conjunction with a suitable pharmaceutical carrier may be administered to a subject to treat or prevent a cell proliferative disorder including, but not limited to, those provided above.

In still another embodiment, an agonist which modulates the activity of HSFM may be administered to a subject to treat or prevent a cell proliferative disorder including, but not limited to, those listed above.

In another embodiment, HSFM or a fragment or derivative thereof may be administered to a subject to treat or prevent an inflammatory disorder. Such inflammatory disorders can include, but are not limited to, acquired immunodeficiency syndrome (AIDS), Addison's disease, adult respiratory distress syndrome, allergies, ankylosing spondylitis, amyloidosis, anemia, asthma, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing HSFM or a fragment or derivative thereof may be administered to a subject to treat or prevent an inflammatory disorder including, but not limited to, those described above.

In a further embodiment, a pharmaceutical composition comprising a substantially purified HSFM in conjunction with a suitable pharmaceutical carrier may be administered to a subject to treat or prevent an inflammatory disorder including, but not limited to, those provided above.

In still another embodiment, an agonist which modulates the activity of HSFM may be administered to a subject to treat or prevent an inflammatory disorder including, but not limited to, those listed above.

In another embodiment, HSFM or a fragment or derivative thereof may be administered to a subject to treat or prevent a fatty acid and steroid metabolic disorder. Such fatty acid and steroid metabolic disorders can include, but are not limited to, fatty hepatocirrhosis, hyperadrenalism, hypoadrenalism, hyperparathyroidism, hypoparathyroidism, hypercholesterolemia, hyperthyroidism, hypothyroidism, hyperlipidemia, hyperlipemia, lipid myopathies, obesity, lipodystrophies, 2,4-dienoyl-CoA reductase deficiency, acyl-CoA oxidase deficiency, thiolase deficiency, peroxisomal bifunctional protein deficiency, mitochondrial camitine palmitoyl transferase and carnitine deficiency, mitochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, and mitochondrial short-chain 3-hydroxyacyl-CoA dehydrogenase deficiency.

In another embodiment, a vector capable of expressing HSFM or a fragment or derivative thereof may be administered to a subject to treat or prevent a fatty acid and steroid metabolic disorder including, but not limited to, those described above.

In a further embodiment, a pharmaceutical composition comprising a substantially purified HSFM in conjunction with a suitable pharmaceutical carrier may be administered to a subject to treat or prevent a fatty acid and steroid metabolic disorder including, but not limited to, those provided above.

In still another embodiment, an agonist which modulates the activity of HSFM may be administered to a subject to treat or prevent a fatty acid and steroid metabolic disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSFM may be produced using methods which are generally known in the art. In particular, purified HSFM may be used to produce antibodies or to screen libraries of pharmaceutical agents to identify those which specifically bind HSFM. Antibodies to HSFM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with HSFM or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) *Antibodies: A Laboratory Manual,* Cold Spring Harbor Laboratory, Cold Spring Harbor, N.Y.)

It is preferred that the oligopeptides, peptides, or fragments used to induce antibodies to HSFM have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of HSFM amino acids may be fused with those of another protein, such as KLH, and antibodies to the chimeric molecule may be produced.

Monoclonal antibodies to HSFM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256: 495–497; Kozbor, D. et al. (1985) J. Immunol. Methods 81: 31–42; Cote, R. J. et al. (1983) Proc. Natl. Acad. Sci. 80: 2026–2030; and Cole, S. P. et al. (1984) Mol. Cell Biol. 62: 109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81: 6851–6855; Neuberger, M. S. et al. (1984) Nature 312: 604–608; and Takeda, S. et al. (1985) Nature 314: 452–454.) Alternatively, techniques described for the production of single chain antibodies may be adapted, using methods known in the art, to produce HSFM-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88: 10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349: 293–299.)

Antibody fragments which contain specific binding sites for HSFM may also be generated. For example, such fragments include, but are not limited to, F(ab)2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246: 1275–1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between HSFM and its specific antibody. A two-site, monoclonal-based immunoassay utilizing monoclonal antibodies reactive to two non-interfering HSFM epitopes is preferred, but a competitive binding assay may also be employed. (Maddox, supra.)

Various methods such as Scatchard analysis in conjunction with radioimmunoassay techniques may be used to assess the affinity of antibodies for HSFM. Affinity is expressed as an association constant, $K_a$. which is defined as the molar concentration of HSFM-antibody complex divided by the molar concentrations of free antigen and free antibody under equilibrium conditions. The $K_a$ determined for a preparation of polyclonal antibodies, which are heterogeneous in their affinities for multiple HSFM epitopes, represents the average affinity, or avidity, of the antibodies for HSFM. The $K_a$ determined for a preparation of monoclonal antibodies, which are monospecific for a particular HSFM epitope, represents a true measure of affinity. High-affinity antibody preparations with $K_a$ ranging from about $10^9$ to $10^{12}$ L/mole are preferred for use in immunoassays in which the HSFM-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HSFM, preferably in active form, from the antibody. (Catty, D. (1988) *Antibodies. Volume I: A Practical Approach,* IRL Press, Washington, D.C.; and Liddell, J. E. and Cryer, A. (1991) *A Practical Guide to Monoclonal Antibodies,* John Wiley & Sons, New York, N.Y.)

The titre and avidity of polyclonal antibody preparations may be further evaluated to determine the quality and suitability of such preparations for certain downstream applications. For example, a polyclonal antibody preparation containing at least 1–2 mg specific antibody/ml, preferably 5-10 mg specific antibody/ml, is preferred for use in procedures requiring precipitation of HSFM-antibody complexes. Procedures for evaluating antibody specificity, titer, and avidity, and guidelines for antibody quality and usage in various applications, are generally available. (See, e.g., Catty, supra, and Coligan et al. supra.) In another embodiment of the invention, the polynucleotides encoding HSFM, or any fragment or complement thereof, may be used for therapeutic purposes. In one aspect, the complement of the polynucleotide encoding HSFM may be used in situations in which it would be desirable to block the transcription of the mRNA. In particular, cells may be transformed with sequences complementary to polynucleotides encoding HSFM. Thus, complementary molecules or fragments may be used to modulate HSFM activity, or to achieve regulation of gene function. Such technology is now well known in the art, and sense or antisense oligonucleotides or larger fragments can be designed from various locations along the coding or control regions of sequences encoding HSFM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HSFM. (See, e.g., Sambrook, supra; and Ausubel, supra.) Genes encoding HSFM can be turned off by transforming a cell or tissue with expression vectors which express high levels of a polynucleotide, or fragment thereof, encoding HSFM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HSFM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HSFM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSFM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15: 462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HSFM, antibodies to HSFM, and mimetics, agonists, antagonists, or inhibitors of HSFM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HSFM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HSFM or fragments thereof, antibodies of HSFM, and agonists, antagonists or inhibitors of HSFM, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}$ $ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient', and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSFM may be used for the diagnosis of disorders characterized by expression of HSFM, or in assays to monitor patients being treated with HSFM or agonists, antagonists, or inhibitors of HSFM. Antibodies useful for diagnostic purposes may be prepared in the same manner as described above for therapeutics. Diagnostic assays for HSFM include methods which utilize the antibody and a label to detect HSFM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HSFM, including ELISAs, RIAs, and FACS, are known in the art and provide a basis for diagnosing altered or abnormal levels of HSFM expression. Normal or standard values for HSFM expression are established by combining body fluids or cell extracts taken from normal mammalian subjects, preferably human, with antibody to HSFM under conditions suitable for complex formation. The amount of standard complex formation may be quantitated by various methods, preferably by photometric means. Quantities of HSFM expressed in subject, control, and disease samples from biopsied tissues are compared with the standard values. Deviation between standard and subject values establishes the parameters for diagnosing disease.

In another embodiment of the invention, the polynucleotides encoding HSFM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSFM may be correlated with disease. The diagnostic assay may be used to determine absence, presence, and excess expression of HSFM, and to monitor regulation of HSFM levels during therapeutic intervention.

In one aspect, hybridization with PCR probes which are capable of detecting polynucleotide sequences, including genomic sequences, encoding HSFM or closely related molecules may be used to identify nucleic acid sequences which encode HSFM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HSFM, allelic variants, or related sequences.

Probes may also be used for the detection of related sequences, and should preferably have at least 50% sequence identity to any of the HSFM encoding sequences. The hybridization probes of the subject invention may be DNA or RNA and may be derived from the sequence of SEQ ID NO:3, SEQ ID NO:4, or from genomic sequences including promoters, enhancers, and introns of the HSFM gene.

Means for producing specific hybridization probes for DNAs encoding HSFM include the cloning of polynucleotide sequences encoding HSFM or HSFM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$p or $^{35}$S, or by enzymatic labels, such as alkaline phosphatase coupled to the probe via avidin/biotin coupling systems, and the like.

Polynucleotide sequences encoding HSFM may be used for the diagnosis of a disorder associated with expression of HSFM. Examples of such a disorder include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders such as acquired immunodeficiency syndrome (AIDS), Addison's disease, adult respiratory distress syndrome, allergies, ankylosing spondylitis, amyloidosis, anemia, asthma, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and fatty acid and steroid metabolic disorders such as fatty hepatocirrhosis, hyperadrenalism, hypoadrenalism, hyperparathyroidism, hypoparathyroidism, hypercholesterolemia, hyperthyroidism, hypothyroidism, hyperlipidemia, hyperlipemia, lipid myopathies, obesity, lipodystrophies, 2,4-dienoyl-CoA reductase deficiency, acyl-CoA oxidase deficiency, thiolase deficiency, peroxisomal bifunctional protein deficiency, mitochondrial carnitine palmitoyl transferase and carnitine deficiency, mitochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, and mitochondrial short-chain 3-hydroxyacyl-CoA dehydrogenase deficiency. The polynucleotide sequences encoding HSFM may be used in Southern or Northern analysis, dot blot, or other membrane-based technologies; in PCR technologies; in dipstick, pin, and ELISA assays; and in microarrays utilizing fluids or tissues from patients to detect altered HSFM expression. Such qualitative or quantitative methods are well known in the art.

In a particular aspect, the nucleotide sequences encoding HSFM may be useful in assays that detect the presence of associated disorders, particularly those mentioned above. The nucleotide sequences encoding HSFM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HSFM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HSFM, a normal or standard profile for expression is established. This may be accomplished by combining body fluids or cell extracts taken from normal subjects, either animal or human, with a sequence, or a fragment thereof, encoding HSFM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSFM may involve the use of PCR. These oligomers may be chemically synthesized, generated enzymatically, or produced in vitro. Oligomers will preferably contain a fragment of a polynucleotide encoding HSFM, or a fragment of a polynucleotide complementary to the polynucleotide encoding HSFM, and will be employed under optimized conditions for identification of a specific gene or condition. Oligomers may also be employed under less stringent conditions for detection or quantitation of closely related DNA or RNA sequences.

Methods which may also be used to quantitate the expression of HSFM include radiolabeling or biotinylating nucleotides, coamplification of a control nucleic acid, and interpolating results from standard curves. (See, e.g., Melby, P. C. et al. (1993) J. Immunol. Methods 159: 235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93: 10614–10619; Baldeschweiler et al. (1995) PCT application WO95/251116; Shalon, D. et al. (1 995) PCT application WO95/35505; Heller, R. A. et al. (1997) Proc. Natl. Acad. Sci. 94: 2150–2155; and Heller, M. J. et al. (1997) U.S. Pat. No. 5,605,662.)

In another embodiment of the invention, nucleic acid sequences encoding HSFM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7: 127–134; and Trask, B. J. (1991) Trends Genet. 7: 149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology,* VCH Publishers New York, N.Y., pp. 965–968.) Examples of genetic map data can be found in various scientific journals or at the Online Mendelian Inheritance in Man (OMIM) site. Correlation between the location of the gene encoding HSFM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11 q22–23, any sequences mapping to that area may represent associated or regulatory genes for further investigation. (See, e.g., Gatti, R. A. et al. (1988) Nature 336: 577–580.) The nucleotide sequence of the subject invention may also be used to detect differences in the chromosomal location due to translocation, inversion, etc., among normal, carrier, or affected individuals.

In another embodiment of the invention, HSFM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HSFM and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HSFM, or fragments thereof, and washed. Bound HSFM is then detected by methods well known in the art. Purified HSFM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSFM specifically compete with a test compound for binding HSFM. In this manner, antibodies can be used to detect the presence of any peptide which shares one or more antigenic determinants with HSFM.

In additional embodiments, the nucleotide sequences which encode HSFM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

LUNGNOT14

The LUNGNOT14 cDNA library was constructed using RNA isolated from lung tissue removed from the left lower lobe of a 47-year-old Caucasian male during a segmental lung resection. Pathology for the associated tumor tissue indicated a grade 4 adenocarcinoma, and the parenchyma showed calcified granuloma. Patient history included benign hypertension, chronic obstructive pulmonary disease, and alcohol abuse. Family history included type II diabetes and acute myocardial infarction.

PROSTUT12

The PROSTUT12 cDNA library was constructed using RNA isolated from prostate tumor tissue from a 65-year-old Caucasian male during a radical prostatectomy. Pathology indicated an adenocarcinoma (Gleason grade 2+2). Adenofibromatous hyperplasia was also present. The patient presented with elevated prostate specific antigen (PSA).

LUNGNOT14 and PROSTUT12

The frozen tissue was homogenized and lysed in guanidinium isothiocyanate solution using a Brinkmann Homogenizer Polytron PT-3000 (Brinkmann Instruments, Westbury, N.Y.). The lysates were centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with acid phenol, precipitated using sodium acetate and ethanol, resuspended in RNAse-free water, and treated with DNase. The RNA was extracted with acid phenol and precipitated as before. Poly(A+) RNA was isolated using the Qiagen Oligotex kit (QIAGEN, Inc., Chatsworth, Calif.).

Poly(A+) RNA was used for cDNA synthesis and library construction according to the recommended protocols in the SuperScript™ plasmid system (Life Technologies, Inc., Gaithersburg, Md.). cDNAs were fractionated on a Sepharose CL4B column (Pharmacia) and those cDNAs exceeding 400 bp were ligated into the pINCY (Incyte Pharmaceuticals, Inc., Palo Alto, Calif.) cloning vector and subsequently transformed into DH5α™ competent cells (Cat. #18258-012, Life Technologies, Inc.).

II. Isolation of cDNA Clones

Plasmid DNA was released from the cells and purified using the REAL Prep 96 plasmid kit (QIAGEN, Inc.). The recommended protocols were employed except for the following changes: 1) the bacteria were cultured in 1 ml of sterile Terrific Broth (Life Technologies, Inc.) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were resuspended in 0.1 ml of distilled water. The DNA samples were stored at 4° C.

The cDNAs were sequenced by the method of Sanger et al. (1975, *J. Mol. Biol.* 94: 441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems, and the reading frame was determined.

III. Similarity Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36: 290–300; and Altschul et al. (1990) J. Mol. Biol. 215: 403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5: 35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25: 217–221.) The BLOCKS algorithm is useful for classifying genes with unknown functions. (Henikoff, S. and Henikoff, G. J., Nucleic Acids Research (1991) 19: 6565–6572.) Blocks, which are 3 to 60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37: 417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Cur. Opin. Str. Biol. 6: 361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28: 405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations.

It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1 % false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\%\text{ sequence identity} \times \%\text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding HSFM occurs. Abundance and percent abundance are also reported. Abundance directly reflects the number of times a particular transcript is represented in a cDNA library, and percent abundance is abundance divided by the total number of sequences examined in the cDNA library.

V. Extension of HSFM Encoding Polynucleotides

The nucleic acid sequences of Incyte Clones 1511003 and 1810320 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (The Perkin-Elmer Corp., Norwalk, Conn.) and thoroughly mixing the enzyme and reaction mix. PCR was performed using the PTC-200 thermal cycler (MJ Research, Inc., Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent *E. coli cells* (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2×carb). The following day, several colonies were randomly picked from each plate and cultured in 150 µl of liquid LB/2×carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |

-continued

| Step 4 | 72° C. for 90 sec |
| --- | --- |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:3 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:3 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™4.06 software (National Biosciences) and labeled by combining 50 pmol of each oligomer, 250 $\mu$Ci of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, V, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENETM. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270: 467–470; and Shalon, D. et al. (1996) Genome Res. 6: 639–645.) Fluorescent probes are prepared and used for hybridization to the elements on the substrate. The substrate is analyzed by procedures described above.

VIII. Complementary Polynucleotides

Sequences complementary to the HSFM-encoding sequences, or any parts thereof, are used to detect, decrease, or inhibit expression of naturally occurring HSFM. Although use of oligonucleotides comprising from about 15 to 30 base pairs is described, essentially the same procedure is used with smaller or with larger sequence fragments. Appropriate oligonucleotides are designed using OLIGO™4.06 software and the coding sequence of HSFM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSFM-encoding transcript.

IX. Expression of HSFM

Expression and purification of HSFM is achieved using bacterial or virus-based expression systems. For expression of HSFM in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HSFM upon induction with isopropyl beta-D-thiogalactopyranoside (IPTG). Expression of HSFM in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HSFM by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91: 3224–3227; Sandig, V. et al. (1996) Hum. Gene Ther. 7: 1937–1945.)

In most expression systems, HSFM is synthesized as a fusion protein with, e.g., glutathione S-trensferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum,* enables the purification of fusion proteins on immobilized glutathione under conditions that maintain protein activity and antigenicity (Pharmacia, Piscataway, N.J.). Following purification, the GST moiety can be proteolytically cleaved from HSFM at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified HSFM obtained by these methods can be used directly in the following activity assay.

X. Demonstration of HSFM Activity

HSFM activity is demonstrated by the ability to oxidize NADPH to NADP in the presence of substrate. (Kunau and Dommes (1978) Eur. J. Biochem. 91: 533–544.) Substrates include, but are not limited to, all-trans-retinaldehyde and cis-4-dienoyl-CoA. HSFM is preincubated for 10 min. at 37° C. in 60 μM potassium phosphate (pH 7.4), 125 nM NADPH, and 0.2 μM CoASH. The reaction is started by addition of the appropriate substrate (12.5 to 150 μM final concentration). Change in absorbance at 340 nm, due to the oxidation of NADPH to NADP, is measured using a spectrophotometer at 23° C. Units of HSFM activity are expressed as μpmoles of NADP formed per minute. A reaction lacking HSFM is used as a negative control.

XI. Functional Assays

HSFM function is assessed by expressing the sequences encoding HSFM at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of HSFM on gene expression can be assessed using highly purified populations of cells transfected with sequences encoding HSFM and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding HSFM and other genes of interest can be analyzed by Northern analysis or microarray techniques.

XII. Production of HSFM Specific Antibodies

HSFM substantially purified using polyacrylamide gel electrophoresis (PAGE)(see, e.g., Harrington, M. G. (1990) Methods Enzymol. 182: 488–495), or other purification techniques, is used to immunize rabbits and to produce antibodies using standard protocols.

Alternatively, the HSFM amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HSFM Using Specific Antibodies

Naturally occurring or recombinant HSFM is substantially purified by immunoaffinity chromatography using antibodies specific for HSFM. An immunoaffinity column is constructed by covalently coupling anti-HSFM antibody to an activated chromatographic resin, such as CNBr-activated Sepharose (Pharmacia & Upjohn). After the coupling, the resin is blocked and washed according to the manufacturer's instructions.

Media containing HSFM are passed over the immunoaffinity column, and the column is washed under conditions that allow the preferential absorbance of HSFM (e.g., high ionic strength buffers in the presence of detergent). The column is eluted under conditions that disrupt antibody/HSFM binding (e.g., a buffer of pH 2 to pH 3, or a high concentration of a chaotrope, such as urea or thiocyanate ion), and HSFM is collected.

XIV. Identification of Molecules Which Interact with HSFM

HSFM, or biologically active fragments thereof, are labeled with $^{125}$I Bolton-Hunter reagent. (See, e.g., Bolton et al. (1973) Biochem. J. 133: 529.) Candidate molecules previously arrayed in the wells of a multi-well plate are incubated with the labeled HSFM, washed, and any wells with labeled HSFM complex are assayed. Data obtained using different concentrations of HSFM are used to calculate values for the number, affinity, and association of HSFM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding an amino acid sequence comprising SEQ ID NO:1 or SEQ ID NO:2.

2. An isolated and purified polynucleotide having a sequence which is complementary to the polynucleotide sequence of claim 1.

3. An isolated and purified polynucleotide comprising a polynucleotide sequence selected from the group consisting of SEQ ID NO:3 and SEQ ID NO:4.

4. An isolated and purified polynucleotide having a sequence which is complementary to the polynucleotide of claim 3.

5. An expression vector containing the polynucleotide of claim 1.

6. A host cell comprising the expression vector of claim 5.

7. A method of producing a polypeptide comprising SEQ ID NO: 1 or SEQ ID NO:2, the method comprising the steps of:

(a) culturing the host cell of claim 6 under conditions suitable for the expression of the polypeptide; and (b) recovering the polypeptide from the host cell culture.

8. A method for detecting a polynucleotide encoding the polypeptide comprising the amino acid sequence from the group consisting of SEQ ID NO:1 and SEQ ID NO:2 in a sample, the method comprising the steps of:

(a) hybridzing the polynucleotide of claim 6 under conditions of high stringency to at least one of the nucleic acids in the sample, thereby forming a hybridization complex; and (b) detecting the hybridization complex, wherein the presence of the hybridization complex correlates with the presence of the polynucletide encoding the polypeptide in the sample.

9. The method of claim 8 further comprising amplifying the polynucleotide prior to the hybridizing step.

10. A isolated and purified fragment of the polynucleotide of claim 3 comprising nucleotide 534 to nucleotide 554 of SEQ ID NO:3, or nucleotide 539 to nucleotide 559 of SEQ ID NO:4.

11. An isolated and purified polynucleotide having a sequence which is completely complementary to the polynucleotide of claim 10.

* * * * *

UNITED STATES PATENT AND TRADEMARK OFFICE
CERTIFICATE OF CORRECTION

PATENT NO. : 6,057,140
DATED : May 2, 2000
INVENTOR(S) : Preeti Lal, Karl J. Guegler, Gina A. Gorgone, Neil C. Corley, Mariah R. Baughn, Henry Yue It is certified that error appears in the above-identified patent and that said Letters Patent are hereby corrected as shown below:

Col. 64, line 28, delete "sequence from" and insert --sequence selected from--

Signed and Sealed this

Fifteenth Day of May, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 309 amino acids
      (B) TYPE: amino acid
      (C) STRANDEDNESS: single
      (D) TOPOLOGY: linear (vii) IMMEDIATE SOURCE:
      (A) LIBRARY: LUNGNOT14
      (B) CLONE: 1511003

(xi) SEQUENCE DESCRIPTION: SEQ ID NO: 1 :

```
Met Ser Phe Asn Leu Gln Ser Ser Lys Lys Leu Phe Ile Phe Leu
                 5                  10                  15

Gly Lys Ser Leu Phe Ser Leu Leu Glu Ala Met Ile Phe Ala Leu
                20                  25                  30

Leu Pro Lys Pro Arg Lys Asn Val Ala Gly Glu Ile Val Leu Ile
                35                  40                  45

Thr Gly Ala Gly Ser Gly Leu Gly Arg Leu Leu Ala Leu Gln Phe
                50                  55                  60

Ala Arg Leu Gly Ser Val Leu Val Leu Trp Asp Ile Asn Lys Glu
                65                  70                  75

Gly Asn Glu Glu Thr Cys Lys Met Ala Arg Glu Ala Gly Ala Thr
                80                  85                  90

Arg Val His Ala Tyr Thr Cys Asp Cys Ser Gln Lys Glu Gly Val
                95                 100                 105

Tyr Arg Val Ala Asp Gln Val Lys Lys Glu Val Gly Asp Val Ser
               110                 115                 120

Ile Leu Ile Asn Asn Ala Gly Ile Val Thr Gly Lys Lys Phe Leu
               125                 130                 135

Asp Cys Pro Asp Glu Leu Met Glu Lys Ser Phe Asp Val Asn Phe
               140                 145                 150

Lys Ala His Leu Trp Thr Tyr Lys Ala Phe Leu Pro Ala Val Ile
               155                 160                 165

Ala Asn Asp His Gly His Leu Val Cys Ile Ser Ser Ser Ala Gly
               170                 175                 180

Leu Ser Gly Val Asn Gly Leu Ala Asp Tyr Cys Ala Ser Lys Phe
               185                 190                 195

Ala Ala Phe Gly Phe Ala Glu Ser Val Phe Val Glu Thr Phe Val
               200                 205                 210

Gln Lys Gln Lys Gly Ile Lys Thr Thr Ile Val Cys Pro Phe Phe
               215                 220                 225

Ile Lys Thr Gly Met Phe Glu Gly Cys Thr Thr Gly Cys Pro Ser
               230                 235                 240

Leu Leu Pro Ile Leu Glu Pro Lys Tyr Ala Val Glu Lys Ile Val
               245                 250                 255

Glu Ala Ile Leu Gln Glu Lys Met Tyr Leu Tyr Met Pro Lys Leu
               260                 265                 270

Leu Tyr Phe Met Met Phe Leu Lys Ser Phe Leu Pro Leu Lys Thr
               275                 280                 285
```

-continued

```
Gly Leu Leu Ile Ala Asp Tyr Leu Gly Ile Leu His Ala Met Asp
            290                 295                 300

Gly Phe Val Asp Gln Lys Lys Leu
            305
```

(2) INFORMATION FOR SEQ ID NO:   2:

(i) SEQUENCE CHARACTERISTICS:
        (A) LENGTH: 292 amino acids
        (B) TYPE: amino acid
        (C) STRANDEDNESS: single
        (D) TOPOLOGY: linear (vii) IMMEDIATE SOURCE:
        (A) LIBRARY: PROSTUT12
        (B) CLONE: 1810320

(xi) SEQUENCE DESCRIPTION: SEQ ID NO: 2 :

```
Met Ala Gln Pro Pro Asp Val Glu Gly Asp Asp Cys Leu Pro
              5                  10                  15

Ala Tyr Arg His Leu Phe Cys Pro Asp Leu Leu Arg Asp Lys Val
             20                  25                  30

Ala Phe Ile Thr Gly Gly Ser Gly Ile Gly Phe Arg Ile Ala
             35                  40                  45

Glu Ile Phe Met Arg His Gly Cys His Thr Val Ile Ala Ser Arg
             50                  55                  60

Ser Leu Pro Arg Val Leu Thr Ala Ala Arg Lys Leu Ala Gly Ala
             65                  70                  75

Thr Gly Arg Arg Cys Leu Pro Leu Ser Met Asp Val Arg Ala Pro
             80                  85                  90

Pro Ala Val Met Ala Ala Val Asp Gln Ala Leu Lys Glu Phe Gly
             95                 100                 105

Arg Ile Asp Ile Leu Ile Asn Cys Ala Ala Gly Asn Phe Leu Cys
            110                 115                 120

Pro Ala Gly Ala Leu Ser Phe Asn Ala Phe Lys Thr Val Met Asp
            125                 130                 135

Ile Asp Thr Ser Gly Thr Phe Asn Val Ser Arg Val Leu Tyr Glu
            140                 145                 150

Lys Phe Phe Arg Asp His Gly Gly Val Ile Val Asn Ile Thr Ala
            155                 160                 165

Thr Leu Gly Asn Arg Gly Gln Ala Leu Gln Val His Ala Gly Ser
            170                 175                 180

Ala Lys Ala Ala Val Asp Ala Met Thr Arg His Leu Ala Val Glu
            185                 190                 195

Trp Gly Pro Gln Asn Ile Arg Val Asn Ser Leu Ala Pro Gly Pro
            200                 205                 210

Ile Ser Gly Thr Glu Gly Leu Arg Arg Leu Gly Gly Pro Gln Ala
            215                 220                 225

Ser Leu Ser Thr Lys Val Thr Ala Ser Pro Leu Gln Arg Leu Gly
            230                 235                 240

Asn Lys Thr Glu Ile Ala His Ser Val Leu Tyr Leu Ala Ser Pro
            245                 250                 255

Leu Ala Ser Tyr Val Thr Gly Ala Val Leu Val Ala Asp Gly Gly
            260                 265                 270

Ala Trp Leu Thr Phe Pro Asn Gly Val Lys Gly Leu Pro Asp Phe
            275                 280                 285

Ala Ser Phe Ser Ala Lys Leu
```

(2) INFORMATION FOR SEQ ID NO:  3:

(i) SEQUENCE CHARACTERISTICS:
        (A) LENGTH: 1269 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT14
        (B) CLONE: 1511003

(xi) SEQUENCE DESCRIPTION: SEQ ID NO: 3 :

```
gccagggact cggtgcctg gggcagacga ggccggcttc tccgcggaca gctagggaga    60
gtgtcctggg tgtcagccag aacatgtctt tcaacctgca atcatcaaag aaactgttca   120
ttttcttagg aaaatcactg tttagtcttc tggaggctat gatttttgcc ttactcccaa   180
agccacggaa gaacgttgct ggtgaaatag tcctcatcac aggtgctgga agtggactcg   240
gaaggctctt agccttgcag tttgcccggc tgggatctgt tcttgttctc tgggatatca   300
ataaggaggg gaatgaggaa acatgtaaga tggctcggga agctggagcc acaagagtgc   360
acgcctatac ctgcgattgc agccaaaagg aaggagtgta tagagtagcc gaccaggtta   420
aaaagaagt cggcgatgtt tccatcctaa tcaacaatgc cggaatcgta acaggcaaaa    480
agttccttga ctgtccagat gagcttatgg aaaagtcatt tgatgtgaat tcaaagcac    540
atttatggac ttataaagcc tttctacctg ctgtgattgc taatgaccat ggacatttgg   600
tttgcatttc aagttcagct ggattaagtg gagTAAATGG gctggcagat tactgTGCAA   660
GTAAATTtgc agcctttggg tttgctGAAT CTGTATTTGT AGAAACATTT gtccaaaaac   720
aaaagggat caaaaccacg attgtgtgcc cctttttat AAAAACTGGa atgtttgaaG     780
GTTGTACTAC AGGCTGTCCT TCTCTGTTGC CAATTCTGGa acCAAAATAT GCAGTTGAAA   840
AAATAGTAGA AGCTATTCTA CAAGAAAAAA TGTACTTGTA TATGCCAAAG TTGTTATACT   900
TCATGATGTT TCTTAAAAGC TTTTTGCCCC TCAAGACAGG ACTGCTTATA GCTGACTATT   960
TGGGCATCCT TCATGCAATG GATGGCTTTG TTGACCAAAA GAAGAAGCTC TAAAGACCAA  1020
CTCTATGGCT AAGGTCATCT GATACACAGT GTTACATAAT GCGTACTTCA ATGAAGAAAA  1080
GTATTTTTGT CTGACAGTGG AATATATCTG GAGACCACAA GTACCACTCC TATTCTGTTA  1140
TCTGGACTAG AATTTTCAAT CAATGTGTTT GAAAATAATG TTGCTATCAC CTATTTGGTT  1200
gagttttggt ttttctttt tcttttttt tccaaAAATA Aagacagccc attttttgtca  1260
tttccatta                                                         1269
```

(2) INFORMATION FOR SEQ ID NO:  4:

(i) SEQUENCE CHARACTERISTICS:
        (A) LENGTH: 1554 base pairs
        (B) TYPE: nucleic acid
        (C) STRANDEDNESS: single
        (D) TOPOLOGY: linear (vii) IMMEDIATE SOURCE:
        (A) LIBRARY: PROSTUT12
        (B) CLONE: 1810320

(xi) SEQUENCE DESCRIPTION: SEQ ID NO: 4 :

```
CTCCCGGTTC CAGGCGAGTT CGCAGCTGCG CGCCGGGTCC TGGAGGCCGA GGCCGCTCCC    60
GCCCGTTGTC CCCGCAGTCC CCGACGGGAG CGCCATGGCC CAGCCGCCGC CCGACGTGGA   120
```

-continued

```
GGGGGACGAC TGTCTCCCCG CGTACCGCCA CCTCTTCTGC CCGGACCTGC TGCGGGACAA      180

AGTGGCCTTC ATCACAGGAG GCGGCTCTGG GATTGGGTTC CGGATTGCTG AGATTTTCAT      240

GCGGCACGGC TGCCATACGG TGATTGCCAG TAGGAGCCTG CCGCGAGTGC TGACGGCCGC      300

CAGGAAGCTG GCTGGGGCCA CCGGCCGGCG CTGCCTCCCT CTCTCTATGG ACGTCCGAGC      360

GCCCCCAGCT GTCATGGCCG CCGTGGACCA GGCTCTGAAG GAGTTTGGCA GAATCGACAT      420

TCTCATTAAC TGTGCGGCCG GGAACTTCCT GTGCCCCGCT GGCGCCTTGT CCTTCAACGC      480

CTTCAAGACC GTGATGGACA TCGATACCAG CGGCACCTTC AATGTGTCTC GTGTGCTCTA      540

TGAGAAGTTC TTCCGGGACC ACGGAGGGGT GATCGTGAAC ATCACTGCCA CCCTGGGGAA      600

CCGGGGGCAG GCGCTCCAGG TGCATGCAGG CTCCGCCAAG GCCGCTGTGG ACGCGATGAC      660

GCGGCACTTG GCTGTGGAGT GGGGTCCCCA AAACATCCGC GTCAACAGCC TCGCCCCTGG      720

CCCCATCAGT GGCACAGAGG GGCTCCGGCG ACTGGGTGGC CCTCAGGCCA GCCTGAGCAC      780

CAAGGTCACT GCCAGCCCGC TGCAGAGGCT GGGGAACAAG ACCGAGATCG CCCACAGCGT      840

GCTCTACCTG GCCAGCCCTC TGGCTTCCTA CGTGACGGGG GCCGTGCTGG TGGCCGATGG      900

CGGGGCATGG TTGACGTTCC CAAACGGTGT CAAAGGGCTG CCGGATTTCG CATCCTTCTC      960

TGCTAAGCTC TAGGAATCTT CCGGCCGCTG CTTCCTGCCG CCTCACTCAG CCAGGTGGAG     1020

AGCACCAATC TGAACCAGCA ATGCCTGCAG CCCAGCCCCT CCTCTGAACA CTCAGCTATT     1080

ACTGCGCTTT CCCTCCCCAC GGCCCCAACT CCAGGGCAGG AGCAACTGGA CAGTGGGCCT     1140

GGCCCGTGGA GCTGCCACGC AGGTGCCTGA GGGCCAGGTG CCACGCAGGT GTCTGAGGAC     1200

CAGGTGCCAC GCAGGTGGTG GGGGTACAGA CAAGATGCTG GGATGTCCCC TGCCCCATGG     1260

TCAAGGGTGT CCTGCCTGCC TGGGTCCAGG GCCTGAGGGA GCCACATGGA TCCCGAGACT     1320

TGTGTTCTCT TGGCTGAAAA CACTGAGGTG CTCCCATCTG TGCGTGGCCC ATGAGCTGGG     1380

ATGGTCCTCC AGCTGCCCAC AAGGTCCGCC CCTCTGTCTC TGCACCACCT GTTTGCATAA     1440

ACACACTTTG CTACAATCTT GCTAGTGCGT TTTCTTAAAA GATAATCTAT TTACTGTAAA     1500

AATAAATTGG ACTTTGCAAA AGCTTTTAGA AGGAAAAGAA AGAGGATTAA AGGG          1554
```

(2) INFORMATION FOR SEQ ID NO: 5:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT14
        (B) CLONE: 1511003F6

(xi) SEQUENCE DESCRIPTION: SEQ ID NO: 5 :

```
GCAGTTTGCC CGGCTGGGAT CTGTTCTTGT TCTCTGGGAT ATCAATAAGG AGGGGAATGA       60

GGAAACATGT AAGATGGCTC GGGAAGCTGG AGCCACAAGA GTGCACGCCT ATACCTGCGA      120

TTGCAGCCAA AAGGAAGGAG TGTATAGAGT AGCCGACCAG GTTAAAAAAG AAGTCGGCGA      180

TGTTTCCATC CTAATCAACA ATGCCGGAAT CGTAACAGGC AAAAAGTTCC TTGACTGTCC      240

AGATGAGCTT ATGGAAAAGT CATTTGATGT GAATTTCAAA GCACATTTAT GGACTTATAA      300

AGCCTTTCTA CCTGCTGTGA TTGCTAATGA CCATGGACAT TTGGTTTGCA TTTCAAGTTC      360

AGCTGGATTA AGTGGAGTAA ATGGGCTGGC AGATTACTGT GCAAGTAAAT TTGCAGCCTT      420

TGGGTTTGCT GAATCTGTAT TTGTAGAAAC ATTTGTCCAA AAACAAAAGG GGATCAAAAC      480
```

```
CACGATTGTG TGCCCCTTTT TTATAAAAAC TGGAATGNTT GAAGGTTGTA CTACAGGCTG    540

TCCTTCCCNG TTGCCAATTC CGGAACCAAA TATGCCGTTG                          580

(2) INFORMATION FOR SEQ ID NO:     6:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT14
        (B) CLONE: 1511003H1

(xi) SEQUENCE DESCRIPTION: SEQ ID NO: 6 :

GCAGTTTGCC CGGCTGGGAT CTGTTCTTGT TCTCTGGGAT ATCAATAAGG AGGGGAATGA    60

GGAAACATGT AAGATGGCTC GGGAAGCTGG AG                                  92

(2) INFORMATION FOR SEQ ID NO:     7:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT14
        (B) CLONE: 1511003T6

(xi) SEQUENCE DESCRIPTION: SEQ ID NO: 7 :

CCNACCNTNG NTTTCAAACA TATNCATTGA AAATTCTAGT CCAGATAACA GAATAGGAGT    60

GGTACTTGTG GTCTCCAGAT ATATTCCACT GTCAGACAAA AATACTTTTC TTCATTGAAG   120

TACGCATTAT GTAACACTGT GTATCAGATG ACCTTAGCCA TAGAGTTGGT CTTTAGAGCT   180

TCTTCTTTTG GTCAACAAAG CCATCCATTG CATGAAGGAT GCCCAAATAG TCAGCTATAA   240

GCAGTCCTGT CTTGAGGGGC AAAAAGCTTT TAAGAAACAT CATGNAGTAT AACAACTTTG   300

GCATATNCNN GTACATTTTN TCTTGTAGAA TAGGCTTCTA CTATNTTTTC AACTGCNTAT   360

TTCGGGTTCC AGAATTGGGC AACNAGATGA ANGNCNGCCT GTAGTACAAC CTTCAAAACA   420

NTCNAGGTTT TATNGAANAA AGNNGGCNCA CCAANCGGTG GTGTTGATCC CCCTTTTGGN   480

TTTGTNGGAC NAATGNTTNN TNCAANTNNN CAGNTTTCCG GCAAANCCCA NNAGGNTGNC   540

AAATTTTNCT TGCNCNGTAA TNNTGCCAGC NCNTTTAACT NCACCNTTAT NCCAGCTGNN   600

ACTTGCNNGT GCNNNCCCCA AATGGTCCCT GGGGTCNTTN GGCAACNCAC ANNCCNNGCT   660

CNNAANGGNT TTCNTAAGNC CCTGAATNGG CNCTCNGANT TCCNCCTNCA GNTGGCNTNN   720

CCANNCAGNT CCCTGGGGAN GNTCCAGGG                                     749

(2) INFORMATION FOR SEQ ID NO: 8:

(i) SEQUENCE CHARACTERISTICS:
        (A) LENGTH: 555 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT10
        (B) CLONE: 2722958F6

(xi) SEQUENCE DESCRIPTION: SEQ ID NO: 8 :
```

```
CCTTCTCTGT TGCCAATTCT GGAACCAAAA TATGCAGTTG AAAAAATAGT AGAAGCTATT      60

CTACAAGAAA AAATGTACTT GTATATGCCA AAGTTGTTAT ACTTCATGAT GTTTCTTAAA     120

AGCTTTTTGC CCCTCAAGAC AGGACTGCTT ATAGCTGACT ATTTGGGCAT CCTTCATGCA     180

ATGGATGGCT TTGTTGACCA AAAGAAGAAG CTCTAAAGAC CAACTCTATG CTAAGGTCA      240

TCTGATACAC AGTGTTACAT AATGCGTACT TCAATGAAGA AAAGTATTTT TGTCTGACAG     300

TGGAATATAT CTGGAGACCA CAAGTACCAC TCCTATTCTG TTATCTGGAC TAGAATTTTC     360

AATCAATGTG TTTGAAAATA ATGTTGCTAT CACCTATTTG GTTGAGTTTT GGNTTTTTCT     420

TTTTCTTTTT TTTTCCAAAA ATAAAGACAG CCCATTTTTG TCATTTCCAT TAAAANAACA     480

ANNNANAAAN NNNNNANNNN NNNNNNNNNN NNNNNNNANN NNNNNNNNNN NNNNNNNNNN     540

NNNNNNNNNN NCTTC                                                    555
```

(2) INFORMATION FOR SEQ ID NO:    9:

(i) SEQUENCE CHARACTERISTICS:
       (A) LENGTH: 265 base pairs
       (B) TYPE: nucleic acid
       (C) STRANDEDNESS: single
       (D) TOPOLOGY: linear (vii) IMMEDIATE SOURCE:
       (A) LIBRARY: SININOT04
       (B) CLONE: 2921571H1

(xi) SEQUENCE DESCRIPTION: SEQ ID NO: 9 :

```
GACTCGGGTG CCTGGGGCAG ANGAGGCCGG CTTCTCCGCG GACAGCTAGG GAGAGTGTCC      60

TGGGTGTCAG CCAGAACATG TCTTTCAACC TGCAATCATC AAAGAAACTG TTCATTTTCT     120

TAGGAAAATC ACTGTTTAGT CTTCTGGAGG CTATGATTTT TGCCTTACTC CCAAAGCCAC     180

GGAAGAACGT TGCTGGTGAA ATAGTCCTCA TCACAGGTGC TGGAAGTGGA CTCGGAAGGC     240

TCTTAGCCTT GCAGTTTGCC CGGCT                                         265
```

(2) INFORMATION FOR SEQ ID NO:   10:

(i) SEQUENCE CHARACTERISTICS:
       (A) LENGTH: 214 base pairs
       (B) TYPE: nucleic acid
       (C) STRANDEDNESS: single
       (D) TOPOLOGY: linear (vii) IMMEDIATE SOURCE:
       (A) LIBRARY: PANCTUT01
       (B) CLONE: 1515168H1

(xi) SEQUENCE DESCRIPTION: SEQ ID NO: 10 :

```
CTTGCTGTTC CCAGATGCCT CTCAGGGAAT GAGCTGNNGG ANANGGGAGG GTGCTGGGTC      60

TTGGGGCTCA CGGGGCCTGA GCCTTCTGCT GCCCTCCAGG TGGCCCTCAG GCCAGCCTGA     120

GCACCAAGGT CACTGCCAGC CCGCTGCAGA GGNNCGGGAA CAAGACCGAG ATCGCCCACA     180

GCGTGCTCTA CCTGGCCAGC CCTCTGGCTT CCTA                                214
```

(2) INFORMATION FOR SEQ ID NO:   11:

(i) SEQUENCE CHARACTERISTICS:
       (A) LENGTH: 759 base pairs
       (B) TYPE: nucleic acid
       (C) STRANDEDNESS: single
       (D) TOPOLOGY: linear (vii) IMMEDIATE SOURCE:

(A) LIBRARY: PROSTUT08
            (B) CLONE: 1653184T6

(xi) SEQUENCE DESCRIPTION: SEQ ID NO: 11 :

AAAAGNNTCT NCAATNCTCT TTNTNNNCCT TCTAAAAGCT TTTGCAAAGT CCAATTTATT          60

TTTACAGTAA ATAGATTATC TTTTAAGAAA ANGCACTAGC NAGATTGTAG NAAAGTGTGT         120

TTATGCAAAC AGGTGGTGCN GANACAGAGG GGCGGACCTT GTGGGCAGCT GGAGGNCCAT         180

CCCAGCTCAT GGGCCCACGN ACANATGGGA GCNCCTCAGT GTTTTCAGCC AAGAGAACAC         240

CAGTCTCGGG ATCCCTGNGG NTCCCTCAGG CCCTGGACCC AGGCAGGCAN GACACCCTTG         300

ACCATGGGGC CAGGGNCATC CCNGCATCTT GTCTGCACCC AACACCTGC GGTGGCANTC          360

GAGCnnnnnn nnnnnnnnnn nnnnnnnnnn nnnnnnnnnn nnnnnnnnnn nnnnNNTGTN         420

CACCTAAAAT TCAATTTNCT GGCCGTCGNN TTTACAAANN TCGGTGAACT GGGGAAAAAC         480

CCCTGGGCGT TTACCCCCAA CCTTTAAATT CNGCCCNTTT GNACGNANNG ANTCCCCCCC         540

CNTTNGNGCN CAAGNCTTTG GGCCGGNNAA NCTNAAGACN GACAAACCGG GGACACCCNG         600

GCACCCNGGA NTTNCGGGCG CCCTTTTNGN CNNNNAACCN ANGGTTTTGG GCGGNAAGGC         660

CCTTGNGNNA ATNTGNGNCC GGANNTTGNG GGGCAANAGN NGTNNNCCCC TTNATGTAGA         720

TNCNGGGNGG GGCCNNTTTA AAAGAGCGCN CNGGNNANG                                759

(2) INFORMATION FOR SEQ ID NO:   12:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT01
        (B) CLONE: 1750778T6

(xi) SEQUENCE DESCRIPTION: SEQ ID NO: 12 :

AGCANTTCTC TTTAATCCTC TTTCTTTTCC TTCTAAAAGC TTTTGCAAAG TCCAATTTAT          60

TTTTACAGTA AATAGATTAT CTTTTAAGAA AACGCACTAG CAAGATTGTA GCAAAGTGTG         120

TTTATGCAAA CAGGTGGTGC AGAGACAGAG GGGCGGACCT TGTGGGCAGC TGGAGGACCA         180

TCCCAGCTCA TGGGCCACGC ACAGATGGGA GCACCTCAGT GTTTTCAGCC AAGAGAACAC         240

AAGTCTCGGG ATCCATGTGG CTCCCTCAGG CCCTGGACCC AGGCAGGCAG GACACCCTTG         300

ACCATGGGGC AGGGGACATC CCAGCATCTT GTCTGTACCC CCACCACCTG CGTGGCACCT         360

GGTCCTCAGA CACCTGCGTG GCACCTGGCC CTCAGGCACC TGCGTGGCAG TCCCACGGGG         420

CCAGGCCCCA CTGTCCAGTT GCTCCTGCCC TTGANGTTNG GGGCCNTTGG GGAAGGGAAA         480

NCGCCANTAA TTAAGTTGAG TNGTTCCAGA AGGAANGGGG GCTTGGGNCT NCAAGGCATT         540

TTGCTTGGGT TCCAAGAATT TGGGTGCTTC NTNCCAACCT TTGGGCTTTA ANTTTAAGGC         600

CGGGCCAGGG AAANNCAANC GGGCCCGGGA AAAGAT                                   636

(2) INFORMATION FOR SEQ ID NO:   13:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (vii) IMMEDIATE SOURCE:
        (A) LIBRARY: PROSTUT12

(B) CLONE: 1810320H1

(xi) SEQUENCE DESCRIPTION: SEQ ID NO: 13 :

GGCTCACGGG GCCTGAGCCT TCTGCTGCCC TCCAGGTGGC CCTCAGGCCA GCCTGAGCAC    60

CAAGGTCACT GCCAGCCCGC TGCAGAGGCT GGGGAACAAG ACCGAGATCG CCCACAGCGT   120

GCTCTACCTG GCCAGCCCTC TGGCTTCCTA CGTGACGGGG GCCGTGCTGG TGGCCGATGG   180

CGGGGCATGG TTNCACGTTC CCAAACGGTG TCAAAGGGCT GCCGGATTTC GCATCCTTCT   240

CTGCTAA                                                             247

(2) INFORMATION FOR SEQ ID NO:    14:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (vii) IMMEDIATE SOURCE:
        (A) LIBRARY: THYRNOT08
        (B) CLONE: 2466459T6

(xi) SEQUENCE DESCRIPTION: SEQ ID NO: 14 :

TGTGGTTATG CAAACAGGTG GTGCAGAGAC AGAGGGGCGG ACCTTGTGGG CAGCTGGAGG    60

ACCATCCCAG CTCATGGGCC ACGCACAGAT GGGAGCACCT CAGTGTTTTC AGCCAAGAGA   120

ACACAAGTCT CGGGATCCAT GTGGCTCCCT CAGGCCCTGG ACCCAGGCAG GCAGGACACC   180

CTTGACCATG GGGCAGGGGA CATCCCAGCA TCTTGTCTGT ACCCCCACCA CCTGCGTGGC   240

ACCTGGTCCT CAGACACCTG CGTGGCACCT GGCCCTCAGG CACCTGCGTG GCAGCTCCAC   300

GGGCCAGGCC CACTGTCCAG TTGCTCCTGC CCTGGAGTTG GGGCCGTGGG GAGGGAAAGC   360

GCAGTAATAG CTGAGTGTTC AGAGGAGGGG CTGGGCTGCA GGCATTGCTG GTTCAGATTG   420

GTGCTCTCCA CCTGGCTGAG TGAGGCGGCA GGAAGCAGCG GCCGGAAGAT TCCTAGAGCT   480

TAGCAGAGAA GGATGCGAAA TCCGGCAGCC CTTTGACACC GTTTGGGAAC GTCAACCATG   540

CCCCGCCATC GGCCACCAGC ACGGCCCCCG TCACGTANGA AGCCAGANGG CTNGCCAGTA   600

GAGCACGCTG TTT                                                      613

(2) INFORMATION FOR SEQ ID NO:    15:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (vii) IMMEDIATE SOURCE:
        (A) LIBRARY: HNT2RAT01
        (B) CLONE: 484767X17

(xi) SEQUENCE DESCRIPTION: SEQ ID NO: 15 :

TCCTNTTNNG GACANTNGCG TCTGNTTCCC TCTACNTGTC CTGCCTGCCT GGGNCCACCG    60

CCNAAGGGAG CCACTTGGTA TCCCGAGACT TGTGTTCTCT TGGCTGAAAA CACTGAGGTG   120

CTCCCATCTG TGCGTGGCCC ATGAGCTGGG ATGGTCCTCC AGCTGCCCAC AAGGTCCGCC   180

CCTCTGTCTC TGCACCACCT GTTTGCATAA ACACACTTTG CTACAATCTT GCTAGTGCGT   240

TTTCTTAAAA GATAATCTAT TTACTGTAAA AATAAATTGG ACTTTGCAAA AGCTTTTAGA   300

AGGAAAAGAA AGAGGATTAA AGAGAATTGC TGGTGAAAAA AAAAAAANNN NTTTNNNAGG   360

(2) INFORMATION FOR SEQ ID NO: 16:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAFC01552F1

(xi) SEQUENCE DESCRIPTION: SEQ ID NO: 16 :

CGTCGACCCC GTGGAGCTGC CACGCAGGTG CCTGAGGGCC AGGTGCCACG CAGGTGTCTG      60

AGGACCAGGT GCCACGCAGG TGGTGGGGGT ACAGACAAGA TGCTGGGATG TCNCCTGCCC     120

CATGGTCAAG GGTGTCCTGC CTGCCTGGGT CCAGGGCCTG AGG                       163

(2) INFORMATION FOR SEQ ID NO: 17:

(i) SEQUENCE CHARACTERISTICS:
        (A) LENGTH: 318 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: g1616654

(xi) SEQUENCE DESCRIPTION: SEQ ID NO: 17 :

Met Trp Leu Pro Leu Leu Leu Gly Ala Leu Leu Trp Ala Val Leu
                  5                  10                  15

Trp Leu Leu Arg Asp Arg Gln Ser Leu Pro Ala Ser Asn Ala Phe
                 20                  25                  30

Val Phe Ile Thr Gly Cys Asp Ser Gly Phe Gly Arg Leu Leu Ala
                 35                  40                  45

Leu Gln Leu Asp Gln Arg Gly Phe Arg Val Leu Ala Ser Cys Leu
                 50                  55                  60

Thr Pro Ser Gly Ala Glu Asp Leu Gln Arg Val Ala Ser Ser Arg
                 65                  70                  75

Leu His Thr Thr Leu Leu Asp Ile Thr Asp Pro Gln Ser Val Gln
                 80                  85                  90

Gln Ala Ala Lys Trp Val Glu Met His Val Lys Glu Ala Gly Leu
                 95                 100                 105

Phe Gly Leu Val Asn Asn Ala Gly Val Ala Gly Ile Ile Gly Pro
                110                 115                 120

Thr Pro Trp Leu Thr Arg Asp Asp Phe Gln Arg Val Leu Asn Val
                125                 130                 135

Asn Thr Met Gly Pro Ile Gly Val Thr Leu Ala Leu Leu Pro Leu
                140                 145                 150

Leu Gln Gln Ala Arg Gly Arg Val Ile Asn Ile Thr Ser Val Leu
                155                 160                 165

Gly Arg Leu Ala Ala Asn Gly Gly Gly Tyr Cys Val Ser Lys Phe
                170                 175                 180

Gly Leu Glu Ala Phe Ser Asp Ser Leu Arg Arg Asp Val Ala His
                185                 190                 195

Phe Gly Ile Arg Val Ser Ile Val Glu Pro Gly Phe Phe Arg Thr
                200                 205                 210

Pro Val Thr Asn Leu Glu Ser Leu Glu Lys Thr Leu Gln Ala Cys
                215                 220                 225

```
Trp Ala Arg Leu Pro Pro Ala Thr Gln Ala His Tyr Gly Gly Ala
                230                 235                 240

Phe Leu Thr Lys Tyr Leu Lys Met Gln Gln Arg Ile Met Asn Leu
                245                 250                 255

Ile Cys Asp Pro Asp Leu Thr Lys Val Ser Arg Cys Leu Glu His
                260                 265                 270

Ala Leu Thr Ala Arg His Pro Arg Thr Arg Tyr Ser Pro Gly Trp
                275                 280                 285

Asp Ala Lys Leu Leu Trp Leu Pro Ala Ser Tyr Leu Pro Ala Ser
                290                 295                 300

Leu Val Asp Ala Val Leu Thr Trp Val Leu Pro Lys Pro Ala Gln
                305                 310                 315

Ala Val Tyr (2) INFORMATION FOR SEQ ID NO:   18:

(i) SEQUENCE CHARACTERISTICS:
        (A) LENGTH: 317 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: g841197

(xi) SEQUENCE DESCRIPTION: SEQ ID NO: 18 :

Met Trp Leu Tyr Leu Leu Ala Leu Val Gly Leu Trp Asn Leu Leu
                5                   10                  15

Arg Phe Leu Arg Glu Arg Lys Val Val Ser His Leu Gln Asp Lys
                20                  25                  30

Tyr Val Phe Ile Thr Gly Cys Asp Ser Gly Phe Gly Asn Leu Leu
                35                  40                  45

Ala Arg Gln Leu Asp Arg Arg Gly Met Arg Val Leu Ala Ala Cys
                50                  55                  60

Leu Thr Glu Lys Gly Ala Glu Gln Leu Arg Ser Lys Thr Ser Asp
                65                  70                  75

Arg Leu Glu Thr Val Ile Leu Asp Val Thr Lys Thr Glu Ser Ile
                80                  85                  90

Val Ala Ala Thr Gln Trp Val Lys Glu Arg Val Gly Asn Arg Gly
                95                  100                 105

Leu Trp Gly Leu Val Asn Asn Ala Gly Ile Ser Val Pro Val Gly
                110                 115                 120

Pro Asn Glu Trp Met Arg Lys Lys Asp Phe Ala Ser Val Leu Asp
                125                 130                 135

Val Asn Leu Leu Gly Val Ile Glu Val Thr Leu Asn Met Leu Pro
                140                 145                 150

Leu Val Arg Lys Ala Arg Gly Arg Val Val Asn Ile Ala Ser Thr
                155                 160                 165

Met Gly Arg Met Ser Leu Val Gly Gly Gly Tyr Cys Ile Ser Lys
                170                 175                 180

Tyr Gly Val Glu Ala Phe Ser Asp Ser Leu Arg Arg Glu Leu Thr
                185                 190                 195

Tyr Phe Gly Val Lys Val Ala Ile Ile Glu Pro Gly Gly Phe Lys
                200                 205                 210

Thr Asn Val Thr Asn Met Glu Arg Leu Ser Asp Asn Leu Lys Lys
```

-continued

```
                215                 220                 225
Leu Trp Asp Gln Thr Thr Glu Glu Val Lys Glu Ile Tyr Gly Glu
                230                 235                 240

Lys Phe Gln Asp Ser Tyr Met Lys Ala Met Glu Ser Leu Val Asn
                245                 250                 255

Thr Cys Ser Gly Asp Leu Ser Leu Val Thr Asp Cys Met Glu His
                260                 265                 270

Ala Leu Thr Ser Cys His Pro Arg Thr Arg Tyr Ser Pro Gly Trp
                275                 280                 285

Asp Ala Lys Phe Phe Tyr Leu Pro Met Ser Tyr Leu Pro Thr Phe
                290                 295                 300

Leu Ser Asp Ala Val Ile His Trp Gly Ser Val Lys Pro Ala Arg
                305                 310                 315

Ala Leu (2) INFORMATION FOR SEQ ID NO:    19:

(i) SEQUENCE CHARACTERISTICS:
        (A) LENGTH: 335 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: g1575000

(xi) SEQUENCE DESCRIPTION: SEQ ID NO: 19 :

Met Lys Leu Pro Ala Arg Val Phe Phe Thr Leu Gly Ser Arg Leu
                  5                 10                  15

Pro Cys Gly Leu Ala Pro Arg Arg Phe Phe Ser Tyr Gly Thr Lys
                 20                 25                  30

Ile Leu Tyr Gln Asn Thr Glu Ala Leu Gln Ser Lys Phe Phe Ser
                 35                 40                  45

Pro Leu Gln Lys Ala Met Leu Pro Pro Asn Ser Phe Gln Gly Lys
                 50                 55                  60

Val Ala Phe Ile Thr Gly Gly Gly Thr Gly Leu Gly Lys Gly Met
                 65                 70                  75

Thr Thr Leu Leu Ser Ser Leu Gly Ala Gln Cys Val Ile Ala Ser
                 80                 85                  90

Arg Lys Met Asp Val Leu Lys Ala Thr Ala Glu Gln Ile Ser Ser
                 95                100                 105

Gln Thr Gly Asn Lys Val His Ala Ile Gln Cys Asp Val Arg Asp
                110                115                 120

Pro Asp Met Val Gln Asn Thr Val Ser Glu Leu Ile Lys Val Ala
                125                130                 135

Gly His Pro Asn Ile Val Ile Asn Asn Ala Ala Gly Asn Phe Ile
                140                145                 150

Ser Pro Thr Glu Arg Leu Ser Pro Asn Ala Trp Lys Thr Ile Thr
                155                160                 165

Asp Ile Val Leu Asn Gly Thr Ala Phe Val Thr Leu Glu Ile Gly
                170                175                 180

Lys Gln Leu Ile Lys Ala Gln Lys Gly Ala Ala Phe Leu Ser Ile
                185                190                 195

Thr Thr Ile Tyr Ala Glu Thr Gly Ser Gly Phe Val Val Pro Ser
                200                205                 210
```

-continued

```
Ala Ser Ala Lys Ala Gly Val Glu Ala Met Ser Lys Ser Leu Ala
            215                 220                 225

Ala Glu Trp Gly Lys Tyr Gly Met Arg Phe Asn Val Ile Gln Pro
            230                 235                 240

Gly Pro Ile Lys Thr Lys Gly Ala Phe Ser Arg Leu Asp Pro Thr
            245                 250                 255

Gly Thr Phe Glu Lys Glu Met Ile Gly Arg Ile Pro Cys Gly Arg
            260                 265                 270

Leu Gly Thr Val Glu Glu Leu Ala Asn Leu Ala Ala Phe Leu Cys
            275                 280                 285

Ser Gly Tyr Ala Ser Trp Val Asn Gly Ala Val Ile Lys Phe Asp
            290                 295                 300

Gly Gly Gly Glu Val Leu Ile Ser Gly Glu Gly Asn Asp Leu Arg
            305                 310                 315

Lys Val Thr Lys Glu Gln Trp Asp Thr Ile Glu Glu Leu Ile Arg
            320                 325                 330

Lys Thr Lys Gly Ser
            335
```